United States Patent
Tanaka et al.

(10) Patent No.: US 12,172,978 B2
(45) Date of Patent: Dec. 24, 2024

(54) ETHER COMPOUND AND HARMFUL ARTHROPOD-CONTROLLING COMPOSITION CONTAINING SAME

(71) Applicant: SUMITOMO CHEMICAL COMPANY, LIMITED, Chuo-ku (JP)

(72) Inventors: Ayaka Tanaka, Chuo-ku (JP); Yoshihiko Nokura, Takarazuka (JP); Yuji Nakajima, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 653 days.

(21) Appl. No.: 17/432,120

(22) PCT Filed: Feb. 19, 2020

(86) PCT No.: PCT/JP2020/006576
§ 371 (c)(1),
(2) Date: Aug. 19, 2021

(87) PCT Pub. No.: WO2020/171129
PCT Pub. Date: Aug. 27, 2020

(65) Prior Publication Data
US 2022/0135537 A1    May 5, 2022

(30) Foreign Application Priority Data
Feb. 20, 2019 (JP) ................. 2019-028201

(51) Int. Cl.
| C07D 401/12 | (2006.01) |
| A01N 43/40 | (2006.01) |
| A01N 43/54 | (2006.01) |
| A01N 43/58 | (2006.01) |
| A01P 7/00 | (2006.01) |
| C07D 401/14 | (2006.01) |

(52) U.S. Cl.
CPC ........... C07D 401/12 (2013.01); A01N 43/40 (2013.01); A01N 43/54 (2013.01); A01N 43/58 (2013.01); A01P 7/00 (2021.08); C07D 401/14 (2013.01)

(58) Field of Classification Search
None
See application file for complete search history.

(56) References Cited

U.S. PATENT DOCUMENTS

2020/0181117 A1    6/2020    Mcleod et al.

FOREIGN PATENT DOCUMENTS

| CN | 107074779 A | 8/2017 |
| CN | 107207438 A | 9/2017 |
| EP | 3 202 761 A1 | 8/2017 |
| EP | 3 252 041 A1 | 12/2017 |
| EP | 3 252 042 A1 | 12/2017 |
| JP | 2020-169214 | * 10/2020 |
| WO | WO 00/71536 A1 | 11/2000 |
| WO | WO-2011145669 | * 11/2011 |
| WO | WO 2013/015822 A1 | 1/2013 |
| WO | WO 2013/059648 A1 | 4/2013 |
| WO | WO 2018/101424 A1 | 6/2018 |
| WO | WO 2019/016066 A1 | 1/2019 |

OTHER PUBLICATIONS

Derwent abstract of WO 2011/145669 (Nov. 24, 2011).*
Derwent Abstract of JP 2020-169214 (Oct. 15, 2020).*
Extended European Search Report issued Sep. 14, 2022 in European Patent Application No. 20758452.5, 7 pages.
International Search Report Issued May 26, 2020 in PCT/JP2020/006576 (submitting English translation only), 3 pages.
International Preliminary Report on Patentability and Written Opinion Issued Aug. 10, 2021 in PCT/JP2020/006576 (submitting English translation only), 4 pages.
Communication pursuant to Article 94(3) EPC issued Sep. 4, 2023, in corresponding European Patent Application No. 20 758 452.5, 5 pages.

(Continued)

*Primary Examiner* — John Pak
(74) *Attorney, Agent, or Firm* — Oblon, McClelland, Maier & Neustadt, L.L.P.

(57) ABSTRACT

The present invention provides a compound having an excellent control effect against harmful arthropods, which is represented by formula (I) [wherein $A^1$ represents $CR^{1b}$ etc., $A^2$ represents $CR^{1c}$ etc., T represents a C1-C10 chain hydrocarbon group which is substituted with one or more halogen atoms etc., Q represents an oxygen atom etc., $R^{1a}$, $R^{1b}$ and $R^{1c}$ are identical to or different from each other, and each represents a C1-C6 alkyl group etc., $R^2$ represents a C1-C6 alkyl group etc., $R^3$ represents a C1-C6 chain hydrocarbon group etc., n is 0, 1 or 2, and q is 0, 1, 2 or 3.], as well as a composition for controlling harmful arthropod comprising the same compound, and a method for controlling harmful arthropod comprising applying the same compound.

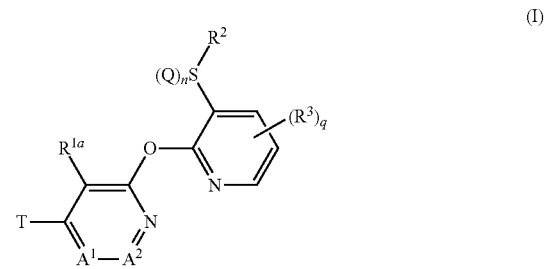

11 Claims, No Drawings

(56) References Cited

OTHER PUBLICATIONS

Combined Chinese Office Action and Search Report issued Sep. 28, 2023, in corresponding Chinese Patent Application No. 202080015229.6 (with English Translation), 21 pages.
Indian First Examination Report issued Apr. 21, 2023 in Indian Patent Application No. 202147038837, 6 pages.
Office Action issued Apr. 12, 2024, in corresponding Chinese Patent Application No. 202080015229.6 (with English Translation), 8 pages.

* cited by examiner

ETHER COMPOUND AND HARMFUL ARTHROPOD-CONTROLLING COMPOSITION CONTAINING SAME

CROSS-REFERENCE TO RELATED APPLICATIONS

This application is a national stage application of PCT/JP2020/006576, filed Feb. 19, 2020, which claims priority to Japanese application 2019-028201, filed Feb. 20, 2019. The contents of all of the above applications are incorporated by reference herein in their entireties.

TECHNICAL FIELD

This application claims priority to and the benefit of Japanese Patent Application No. 2019-028201 filed Feb. 20, 2019, the entire contents of which are incorporated herein by reference.

The present invention relates to an ether compound and a harmful arthropod control composition comprising the same.

BACKGROUND ART

To date, in order to control harmful arthropods, some compounds have been studied. For example, a certain class of compound has been described to have an effect on controlling pests (see Patent Document 1).

CITATION LIST

Patent Document

Patent Document 1: WO 2013/059648

SUMMARY OF THE INVENTION

Problems to be Solved by Invention

An object of the present invention is to provide a compound having an excellent control efficacy against harmful arthropods.

Means to Solve Problems

The present inventors have intensively studied to find out a compound having an excellent control efficacy against a harmful arthropod, and as a result, found that a compound represented by the following formula (I) and so on has an excellent control efficacy against harmful arthropods.

That is, the present invention encompassed the followings.

[1] A compound represented by formula (I):

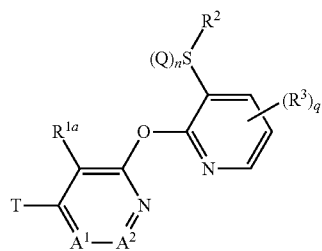

(I)

[wherein
a combination of $A^1$ and $A^2$ represents
  a combination wherein $A^1$ represents a nitrogen atom or $CR^{1b}$ and $A^2$ represents $CR^{1c}$; or
  a combination wherein $A^1$ represents $CR^{1b}$ and $A^2$ represents a nitrogen atom,
$R^{1a}$, $R^{1b}$ and $R^{1c}$ are identical to or different from each other and each represents a C1-C6 alkyl group which may be optionally substituted with one or more halogen atoms, a C1-C6 alkoxy group which may be optionally substituted with one or more halogen atoms, a C1-C6 alkylamino group which may be optionally substituted with one or more halogen atoms, a di(C1-C4 alkyl)amino group which may be optionally substituted with one or more halogen atoms, a hydroxy group, an amino group, a nitro group, a cyano group, a halogen atom, or a hydrogen atom,
$R^2$ represents a C1-C6 alkyl group which may be optionally substituted with one or more halogen atoms, a cyclopropyl group, or a cyclopropylmethyl group,
n is 0, 1 or 2,
q is 0, 1, 2 or 3,
$R^3$ each represents a C1-C6 chain hydrocarbon group which may be optionally substituted with one or more substituents selected from Group A, a C3-C7 cycloalkyl group which may be optionally substituted with one or more substituents selected from Group B, a phenyl group which may be optionally substituted with one or more substituents selected from Group C, a five or six membered aromatic heterocyclic group which may be optionally substituted with one or more substituents selected from Group C, a three to seven membered nonaromatic heterocyclic group which may be optionally substituted with one or more substituents selected from Group B, $OR^8$, $NR^7R^8$, $NR^7NR^8R^9$, $NR^7OR^9$, $NR^7C(O)R^{10}$, $NR^7C(O)OR^{11}$, $N=CHNR^7R^9$, $C(O)R^{10}$, $C(O)OR^{10}$, $C(O)NR^7R^8$, $CR^7=NOR^9$, $S(O)_pR^{12}$, a cyano group, a nitro group, or a halogen atom, and when q is 2 or 3, a plural of $R^3$ may be identical to or different from each other,
p is 0, 1 or 2,
Q represents an oxygen atom or $NR^4$, and when n is 2, two Q may be identical to or different from each other,
$R^4$ represents a C1-C6 alkyl group which may be optionally substituted with one or more halogen atoms, a C2-C7 alkylcarbonyl group which may be optionally substituted with one or more halogen atoms, a C2-C7 alkoxycarbonyl group which may be optionally substituted with one or more halogen atoms, a cyano group, a nitro group, or a hydrogen atom,
T represents a C1-C10 chain hydrocarbon group which is substituted with one or more halogen atoms, $OR^6$, $S(O)_mR^6$, $OS(O)_2R^6$, $NR^6R^7$, a group represented by formula $T^1$, a group represented by formula $T^2$, or a group represented by formula $T^3$,

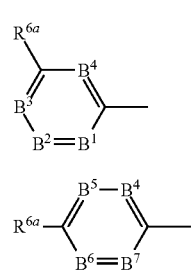

T1

T2

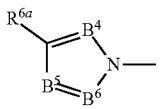

a combination of $B^1$, $B^2$ and $B^3$ represents
a combination wherein $B^1$ represents $CR^{5a}$, $B^2$ represents a nitrogen atom or $CR^{5b}$, and $B^3$ represents a nitrogen atom or $CR^{5c}$; or
a combination wherein $B^1$ represents a nitrogen atom, $B^2$ represents $CR^{5b}$, and $B^3$ represents a nitrogen atom or $CR^{5c}$; or
a combination wherein $B^1$ and $B^2$ represent a nitrogen atom, and $B^3$ represents $CR^{5c}$,
$B^4$ represents a nitrogen atom or $CR^{5d}$,
$B^5$ represents a nitrogen atom or $CR^{5e}$,
$B^6$ represents a nitrogen atom or $CR^{5f}$,
$B^7$ represents a nitrogen atom or $CR^{5g}$,
$R^{5a}$, $R^{5b}$, $R^{5c}$, $R^{5d}$, $R^{5e}$, $R^{5f}$ and $R^{5g}$ are identical to or different from each other and each represent a C1-C6 chain hydrocarbon group which may be optionally substituted with one or more halogen atoms, a C3-C6 cycloalkyl group which may be optionally substituted with one or more halogen atoms, a halogen atom, or a hydrogen atom,
$R^{6a}$ represents a C1-C5 chain hydrocarbon group which is substituted with one or more halogen atoms, $OR^{12}$, $OS(O)_2R^{12}$, $S(O)_mR^{12}$, or a halogen atom,
m is 0, 1 or 2,
$R^{12}$ represents a C1-C6 chain hydrocarbon group which is substituted with one or more halogen atoms,
$R^6$ represents a C1-C10 chain hydrocarbon group which is substituted with one or more substituents selected from the group consisting of cyano group and halogen atom; or a (C3-C7 cycloalkyl) C1-C3 alkyl group which is substituted with one or more substituents selected from the group consisting of cyano group, halogen atom and C1-C6 haloalkyl group,
$R^7$ and $R^9$ are identical to or different from each other and each represent a C1-C6 chain hydrocarbon group which may be optionally substituted with one or more halogen atoms, or a hydrogen atom,
$R^8$ represents a C1-C6 chain hydrocarbon group which may be optionally substituted with one or more substituents selected from Group A, a C3-C7 cycloalkyl group which may be optionally substituted with one or more substituents selected from Group B, a phenyl group which may be optionally substituted with one or more substituents selected from Group C, a five or six membered aromatic heterocyclic group which may be optionally substituted with one or more substituents selected from Group C, a C1-C6 alkylsulfonyl group which may be optionally substituted with one or more halogen atoms, or a hydrogen atom,
$R^{10}$ represents a C1-C6 chain hydrocarbon group which may be optionally substituted with one or more halogen atoms, a C3-C7 cycloalkyl group which may be optionally substituted with one or more halogen atoms, a (C3-C6 cycloalkyl) C1-C3 alkyl group which may be optionally substituted with one or more halogen atoms, a phenyl group which may be optionally substituted with one or more substituents selected from Group C, a five or six membered aromatic heterocyclic group which may be optionally substituted with one or more substituents selected from Group C, or a hydrogen atom,
$R^{11}$ represents a C1-C6 chain hydrocarbon group which may be optionally substituted with one or more halogen atoms, a C3-C7 cycloalkyl group which may be optionally substituted with one or more halogen atoms, a (C3-C6 cycloalkyl) C1-C3 alkyl group which may be optionally substituted with one or more halogen atoms, a phenyl group which may be optionally substituted with one or more substituents selected from Group C, or a five or six membered aromatic heterocyclic group which may be optionally substituted with one or more substituents selected from Group C.
Group A: the group consisting of a C1-C6 alkoxy group which may be optionally substituted with one or more halogen atoms, a C3-C6 alkenyloxy group which may be optionally substituted with one or more halogen atoms, a C3-C6 alkynyloxy group which may be optionally substituted with one or more halogen atoms, a C1-C6 alkylsulfanyl group which may be optionally substituted with one or more halogen atoms, a C1-C6 alkylsulfinyl group which may be optionally substituted with one or more halogen atoms, a C1-C6 alkylsulfonyl group which may be optionally substituted with one or more halogen atoms, a C1-C6 alkylamino group which may be optionally substituted with one or more halogen atoms, a di(C1-C4 alkyl)amino group which may be optionally substituted with one or more halogen atoms, a C3-C6 cycloalkyl group which may be optionally substituted with one or more halogen atoms, a phenyl group, a five or six membered aromatic heterocyclic group {the phenyl group and the five or six membered aromatic heterocyclic group may be optionally substituted with one or more substituents selected from the group consisting of C1-C6 alkyl group which may be optionally substituted with one or more halogen atoms, C1-C6 alkoxy group which may be optionally substituted with one or more halogen atoms, cyano group, nitro group, and halogen atom}, an amino group, a cyano group, a hydroxy group, a sulfanyl group, and a halogen atom.
Group B: the group consisting of a C1-C6 alkyl group which may be optionally substituted with one or more halogen atoms, a halogen atom, and a cyano group.
Group C: the group consisting of a C1-C6 alkyl group which may be optionally substituted with one or more halogen atoms, a C1-C6 alkoxy group which may be optionally substituted with one or more halogen atoms, a C3-C6 alkenyloxy group which may be optionally substituted with one or more halogen atoms, a C3-C6 alkynyloxy group which may be optionally substituted with one or more halogen atoms, a C1-C6 alkylsulfanyl group which may be optionally substituted with one or more halogen atoms, a C1-C6 alkylsulfinyl group which may be optionally substituted with one or more halogen atoms, a C1-C6 alkylsulfonyl group which may be optionally substituted with one or more halogen atoms, a C1-C6 alkylamino group which may be optionally substituted with one or more halogen atoms, a di(C1-C4 alkyl)amino group which may be optionally substituted with one or more halogen atoms, a C2-C7 alkylcarbonyl group which may be optionally substituted with one or more halogen atoms, a C2-C7 alkoxycarbonyl group which may be optionally substituted with one or more halogen atoms, an amino group, a cyano group, a nitro group, a hydroxy group, a sulfanyl group, and a halogen atom]
(hereinafter, referred to "Present compound N" or "Compound N of the present invention") or its N oxide compound (hereinafter, a compound represented by formula (I) or its N oxide compound is referred to as "Present compound" or "Compound of the present invention").

[2] The compound according to [1] or its N oxide compound wherein $A^1$ represents a nitrogen atom or CH, $A^2$ represents CH, and Q represents an oxygen atom.

[3] The compound according to [1] or its N oxide compound wherein $A^1$ and $A^2$ represent CH, and Q represents an oxygen atom.

[4] The compound according to any one of [1] to [3] or its N oxide compound wherein T represents $OR^6$.

[5] The compound according to [4] or its N oxide compound wherein $R^6$ represents a C2-C5 alkyl group which is substituted with one or more halogen atoms.

[6] A composition for controlling a harmful arthropod comprising the compound according to any one of [1] to [5] or its N oxide compound.

[7] A composition which comprises one or more ingredients selected from the group consisting of the following Groups (a), (b), (c) and (d), and the compound according to any one of [1] to [5] or its N oxide compound (hereinafter, the composition is referred to as "Present composition" or "Composition of the present invention"):
  Group (a): a group consisting of insecticidal ingredients, miticidal ingredients, and nematicidal ingredients;
  Group (b): fungicidal ingredients:
  Group (c): plant growth modulating ingredients; and
  Group (d): repellent ingredients.

[8] A method for controlling a harmful arthropod, which comprises applying an effective amount of the compound according to any one of [1] to [5] or its N oxide compound, or an effective amount of the composition according to [7] to a harmful arthropod or a habitat where the harmful arthropod lives.

[9] A seed or vegetative reproductive organ carrying an effective amount of the compound according to any one of [1] to [5] or its N oxide or an effective amount of the composition according to [7].

Effect of Invention

The present invention can control harmful arthropods.

MODE FOR CARRYING OUT THE INVENTION

The substituents as used herein are explained as follows.
The term "halogen atom" represents a fluorine atom, a chlorine atom, a bromine atom, or an iodine atom.
When a substituent is substituted with two or more halogen atoms or substituents, the halogen atoms or the substituents may be identical to or different from each other.
The expression "CX-CY" as used herein represents that the number of carbon atoms is from X to Y. For example, the expression "C1-C6" represents that the number of carbon atoms is from 1 to 6.
The term "chain hydrocarbon group" represents an alkyl group, an alkenyl group, or an alkynyl group.
Examples of "alkyl group" include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group, hexyl group, octyl group, nonyl group, and decyl group.

Examples of "alkenyl group" include vinyl group, 1-propenyl group, 2-propenyl group, 1-methyl-1-propenyl group, 1-methyl-2-propenyl group, 1,2-dimethyl-1-propenyl group, 1-ethyl-2-propenyl group, 3-butenyl group, 4-pentenyl group, 5-hexenyl group, 7-octenyl group, nonenyl group, and decenyl group.

Examples of "alkynyl group" include ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, 7-octynyl group, nonynyl group, and decynyl group.

Examples of "alkoxy group" include methoxy group, ethoxy group, propoxy group, isopropoxy group, butoxy group, tert-butoxy group, pentyloxy group, and hexyloxy group.

Examples of "alkenyloxy group" include 2-propenyloxy group, 2-butenyloxy group, and 5-hexenyloxy group.

Examples of "alkynyloxy group" include 2-propynyloxy group, 2-buthynyloxy group, and 5-hexynyloxy group.

Examples of "alkylamino group" include methylamino group, ethylamino group, propylamino group, and hexylamino group.

Examples of "di(C1-C4 alkyl)amino group" include dimethylamino group, diethylamino group, dibutylamino group, and butylmethylamino group.

Examples of "alkylcarbonyl group" include acetyl group, propanoyl group, butanoyl group, and heptanoyl group.

Examples of "alkoxycarbonyl group" include methoxycarbonyl group, ethoxycarbonyl group, propoxycarbonyl group, and hexyloxycarbonyl group.

Examples of "haloalkyl group" include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

The "alkylsulfanyl group", "alkylsulfinyl group", and "alkylsulfonyl group" represent an alkyl group including an $S(O)_z$ moiety, respectively.

Examples of the "alkylsulfanyl group" when z is 0 include methylsulfanyl group, ethylsulfanyl group, propylsulfanyl group, and isopropylsulfanyl group.

Examples of the "alkylsulfinyl group" when z is 1 include methylsulfinyl group, ethylsulfinyl group, propylsulfinyl group, and isopropylsulfinyl group.

Examples of the "alkylsulfonyl group" when z is 2 include methylsulfonyl group, ethylsulfonyl group, propylsulfonyl group, and isopropylsulfonyl group.

Examples of the "cycloalkyl group" include cyclopropyl group, cyclobutyl group, cyclopentyl group, and cyclohexyl group.

Examples of the "cycloalkenyl group" include cyclopentenyl group, and cyclohexenyl group.

Examples of the "three (3) to seven (7) membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the three to seven membered nonaromatic heterocyclic group which may be optionally one or more substituents selected from Group B include the following groups.

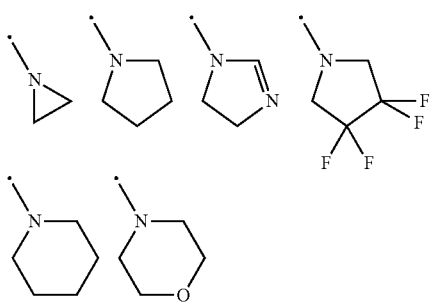

Examples of the "five (5) or six (6) membered aromatic heterocyclic group" include five membered aromatic heterocyclic group such as pyrrolyl group, furanyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group; and six membered aromatic heterocyclic group such as pyridyl group, pyridazinyl group, pyrimidinyl group, pyrazinyl group, triazinyl group, and tetrazinyl group.

Examples of the "(C3-C6 cycloalkyl) C1-C3 alkyl group which may be optionally substituted with one or more halogen atoms" include cyclopropylmethyl group, (2-fluorocyclopropyl)methyl group, cyclopropyl(fluoro)methyl group, and (2-fluorocyclopropyl) (fluoro)methyl group.

The present compound may have one or more stereoisomer(s). Examples of the stereoisomer include enantiomer, diastereomer, and geometric isomer, etc. The present compound includes its each stereoisomer and a mixture of stereoisomers in any ratio.

The present compound may form an acid addition salt. Examples of an acid to form the acid addition salt include inorganic acids such as hydrogen chloride, phosphoric acid and sulfuric acid, and organic acids such as acetic acid, trifluoroacetic acid, benzoic acid and p-toluenesulfonic acid. The acid addition salt can be prepared by mixing the present compound with the acid.

Embodiments of the present compound N include the following compounds.

Embodiment 1

The present compound N wherein $R^3$ represents a C1-C6 chain hydrocarbon group which may be optionally substituted with one or more substituents selected from Group A, a C3-C7 cycloalkyl group which may be optionally substituted with one or more substituents selected from Group B, a phenyl group which may be optionally substituted with one or more substituents selected from Group C, or a halogen atom, and q is 0 or 1.

Embodiment 2

The present compound N wherein $R^3$ represents a C1-C6 alkyl group, a C3-C7 cycloalkyl group {the C1-C6 alkyl group and the C3-C7 cycloalkyl group may be optionally substituted with one or more substituents selected from the group consisting of cyano group and halogen atom}, or a halogen atom, and q is 0 or 1.

Embodiment 3

The present compound N wherein T represents a C1-C6 alkyl group which is substituted with one or more halogen atoms or $OR^6$, and $R^6$ represents a C1-C6 alkyl group which is substituted with one or more substituents selected from the group consisting of cyano group and halogen atom; or a (C3-C7 cycloalkyl) C1-C3 alkyl group which is substituted with one or more substituents selected from the group consisting of cyano group and halogen atom.

Embodiment 4

The compound according to the embodiment 1 wherein T represents a C1-C6 alkyl group which is substituted with one or more halogen atoms or $OR^6$, and $R^6$ represents a C1-C6 alkyl group which is substituted with one or more substituents selected from the group consisting of cyano group and halogen atom; or a (C3-C7 cycloalkyl) C1-C3 alkyl group which is substituted with one or more substituents selected from the group consisting of cyano group and halogen atom.

Embodiment 5

The compound according to the embodiment 2 wherein T represents a C1-C6 alkyl group which is substituted with one or more halogen atoms or $OR^6$, and $R^6$ represents a C1-C6 alkyl group which is substituted with one or more substituents selected from the group consisting of cyano group and halogen atom; or a (C3-C7 cycloalkyl) C1-C3 alkyl group which is substituted with one or more substituents selected from the group consisting of cyano group and halogen atom.

Embodiment 6

The present compound N wherein Q represents an oxygen atom or N—CN.

Embodiment 7

The present compound N wherein each Q represents an oxygen atom, and n is 2.

Embodiment 8

The compound according to the embodiment 1 wherein Q represents an oxygen atom or N—CN.

Embodiment 9

The compound according to the embodiment 2 wherein Q represents an oxygen atom or N—CN.

Embodiment 10

The compound according to the embodiment 3 wherein Q represents an oxygen atom or N—CN.

Embodiment 11

The compound according to the embodiment 4 wherein Q represents an oxygen atom or N—CN.

Embodiment 12

The compound according to the embodiment 5 wherein Q represents an oxygen atom or N—CN.

Embodiment 13

The compound according to the embodiment 1 wherein each Q represents an oxygen atom, and n is 2.

Embodiment 14

The compound according to the embodiment 2 wherein each Q represents an oxygen atom, and n is 2.

Embodiment 15

The compound according to the embodiment 3 wherein each Q represents an oxygen atom, and n is 2.

Embodiment 16

The compound according to the embodiment 4 wherein each Q represents an oxygen atom, and n is 2.

Embodiment 17

The compound according to the embodiment 5 wherein each Q represents an oxygen atom, and n is 2.

Embodiment 18

The present compound N wherein $R^2$ represents a C1-C6 alkyl group.

Embodiment 19

The present compound N wherein $R^2$ represents an ethyl group.

Embodiment 20

The compound according to the embodiment 1 wherein $R^2$ represents a C1-C6 alkyl group.

Embodiment 21

The compound according to the embodiment 2 wherein $R^2$ represents a C1-C6 alkyl group.

Embodiment 22

The compound according to the embodiment 3 wherein $R^2$ represents a C1-C6 alkyl group.

Embodiment 23

The compound according to the embodiment 4 wherein $R^2$ represents a C1-C6 alkyl group.

Embodiment 24

The compound according to the embodiment 5 wherein $R^2$ represents a C1-C6 alkyl group.

Embodiment 25

The compound according to the embodiment 6 wherein $R^2$ represents a C1-C6 alkyl group.

Embodiment 26

The compound according to the embodiment 7 wherein $R^2$ represents a C1-C6 alkyl group.

Embodiment 27

The compound according to the embodiment 8 wherein $R^2$ represents a C1-C6 alkyl group.

Embodiment 28

The compound according to the embodiment 9 wherein $R^2$ represents a C1-C6 alkyl group.

Embodiment 29

The compound according to the embodiment 10 wherein $R^2$ represents a C1-C6 alkyl group.

Embodiment 30

The compound according to the embodiment 11 wherein $R^2$ represents a C1-C6 alkyl group.

Embodiment 31

The compound according to the embodiment 12 wherein $R^2$ represents a C1-C6 alkyl group.

Embodiment 32

The compound according to the embodiment 13 wherein $R^2$ represents a C1-C6 alkyl group.

Embodiment 33

The compound according to the embodiment 14 wherein $R^2$ represents a C1-C6 alkyl group.

Embodiment 34

The compound according to the embodiment 15 wherein $R^2$ represents a C1-C6 alkyl group.

Embodiment 35

The compound according to the embodiment 16 wherein $R^2$ represents a C1-C6 alkyl group.

Embodiment 36

The compound according to the embodiment 17 wherein $R^2$ represents a C1-C6 alkyl group.

Embodiment 37

The compound according to the embodiment 1 wherein $R^2$ represents an ethyl group.

Embodiment 38

The compound according to the embodiment 2 wherein $R^2$ represents an ethyl group.

Embodiment 39

The compound according to the embodiment 3 wherein $R^2$ represents an ethyl group.

Embodiment 40

The compound according to the embodiment 4 wherein $R^2$ represents an ethyl group.

Embodiment 41

The compound according to the embodiment 5 wherein $R^2$ represents an ethyl group.

Embodiment 42

The compound according to the embodiment 6 wherein $R^2$ represents an ethyl group.

Embodiment 43

The compound according to the embodiment 7 wherein $R^2$ represents an ethyl group.

Embodiment 44

The compound according to the embodiment 8 wherein $R^2$ represents an ethyl group.

Embodiment 45

The compound according to the embodiment 9 wherein $R^2$ represents an ethyl group.

Embodiment 46

The compound according to the embodiment 10 wherein $R^2$ represents an ethyl group.

Embodiment 47

The compound according to the embodiment 11 wherein $R^2$ represents an ethyl group.

Embodiment 48

The compound according to the embodiment 12 wherein $R^2$ represents an ethyl group.

Embodiment 49

The compound according to the embodiment 13 wherein $R^2$ represents an ethyl group.

Embodiment 50

The compound according to the embodiment 14 wherein $R^2$ represents an ethyl group.

Embodiment 51

The compound according to the embodiment 15 wherein $R^2$ represents an ethyl group.

Embodiment 52

The compound according to the embodiment 16 wherein $R^2$ represents an ethyl group.

Embodiment 53

The compound according to the embodiment 17 wherein $R^2$ represents an ethyl group.

Embodiment 54

The compound according to any one of the embodiment 1 to the embodiment 53 or the present compound N wherein $A^1$ represents a nitrogen atom or CH, and $A^2$ represents CH.

Embodiment 55

The compound according to any one of the embodiment 1 to the embodiment 53 or the present compound N wherein $A^1$ and $A^2$ represent CH.

Embodiment 56

The compound according to any one of the embodiment 1 to the embodiment 53 or the present compound N wherein $A^1$ represents a nitrogen atom and $A^2$ represents CH.

Next, a process for preparing the compound of the present invention is explained.

Process 1

A compound represented by formula (I-n1QO) (hereinafter, referred to as "Compound (I-n1QO)") or a compound represented by formula (I-n2QO) (hereinafter, referred to as "Compound (I-n2QO)") can be prepared by reacting a compound represented by formula (I-n0) (hereinafter, referred to as "Compound (I-n0)") with an oxidizing agent.

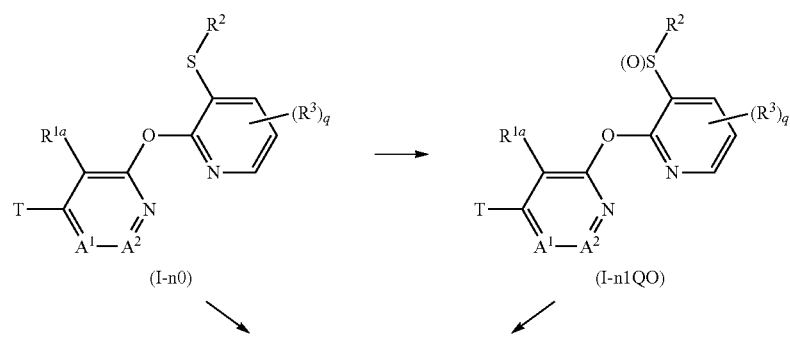

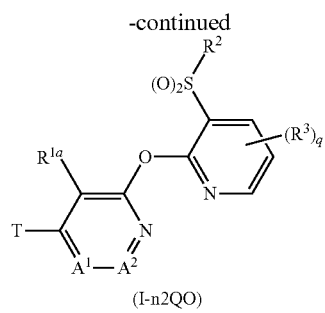

(I-n2QO)

[wherein the symbols are the same as defined above.]

Firstly, a process for the compound (I-n1QO) from the compound (I-n0) is described.

The reaction is usually carried out in a solvent. Examples of the solvents to be used in the reaction include halogenated hydrocarbons such as dichloromethane and chloroform (hereinafter, referred to as "halogenated hydrocarbons"); nitriles such as acetonitrile (hereinafter, referred to as "nitriles"); and alcohols such as methanol and ethanol (hereinafter, referred to as "alcohols"); acetic acid; water; and mixed solvents of these two or more solvents.

Examples of the oxidizing agent to be used in the reaction includes sodium periodate, m-chloroperoxybenzoic acid (hereinafter referred to as "mCPBA"), and hydrogen peroxide.

In the reaction, the oxidizing agent is used usually within a range of 0.8 to 1.2 molar ratios, as opposed to 1 mole of the Present compound (I-n0).

When hydrogen peroxide is used as the oxidizing agent, a base or a catalyst may be added as needed. Examples of the base to be used in the reaction include sodium carbonate. Examples of the catalyst include tungstic acid and sodium tungstate. When the base or the catalyst is used in the reaction, the base is used usually within a range of 0.01 to 1 molar ratio(s), and the catalyst is used within a range of 0.01 to 0.5 molar ratios, as opposed to 1 mole of the compound (I-n0).

The reaction temperature of the reaction is usually within a range of −20 to 80° C. The reaction period of the reaction is usually within a range of 0.1 to 12 hours.

When the reaction is completed, to the reaction mixture is added water, and the reaction mixture are then extracted with organic solvent(s), and the organic layers are washed with an aqueous solution of a reducing agent (such as sodium sulfite, and sodium thiosulfate) and an aqueous solution of a base (such as sodium hydrogen carbonate) as needed. The resulting organic layers are dried and concentrated to obtain the compound (I-n1QO).

Next, a process for preparing the compound (I-n2QO) from the compound (I-n1QO) is described.

The reaction is usually carried out in a solvent. Examples of the solvents to be used in the reaction include halogenated hydrocarbons, nitriles, alcohols, acetic acid, water, and mixed solvents of these two or more solvents.

Examples of the oxidizing agent to be used in the reaction include mCPBA and hydrogen peroxide.

In the reaction, the oxidizing agent is used usually within a range of 0.8 to 2 molar ratios, as opposed to 1 mole of the compound (I-n1QO).

When hydrogen peroxide is used as a hydrogen peroxide, a base or a catalyst may be added as needed. Examples of the base to be used in the reaction include sodium carbonate. Examples of the catalyst include sodium tungstate. When the base or the catalyst is used in the reaction, the base is used usually within a range of 0.01 to 1 molar ratio(s), and the catalyst is used within a range of 0.01 to 0.5 molar ratios, as opposed to 1 mole of the compound (I-n1QO).

The reaction temperature of the reaction is usually within a range of −20 to 120° C. The reaction period of the reaction is usually within a range of 0.1 to 12 hours.

When the reaction is completed, to the reaction mixture is added water, and the reaction mixture are then extracted with organic solvent(s), and the organic layers are washed with an aqueous solution of a reducing agent (such as sodium sulfite, and sodium thiosulfate) and an aqueous solution of a base (such as sodium hydrogen carbonate) as needed. The resulting organic layers are dried and concentrated to obtain the compound (I-n2QO).

Also, the compound (I-2QO) can be prepared by reacting the compound (I-n0) with the oxidizing agent in one step (one-pot).

The reaction can be carried out by using the oxidizing agent in a ratio of usually 2 to 5 molar ratios as opposed to 1 mole of the compound (I-n0), according to the method for preparing the compound (I-n2QO) from the compound (I-n1QO).

Process 2

The compound (I-n0) can be prepared by reacting a compound represented by formula (M-1) (hereinafter, referred to as "Compound (M-1)") with a compound represented by formula (R-1) (hereinafter, referred to as "Compound (R-1)") in the presence of a base.

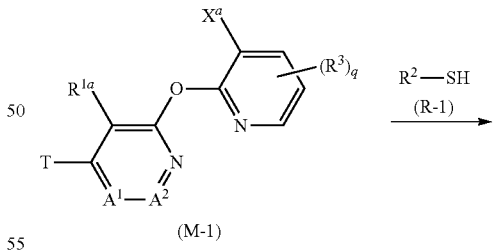

(M-1)

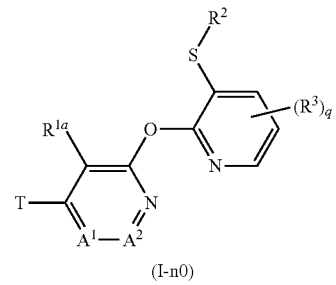

(I-n0)

[wherein, $X^a$ represents a fluorine atom or a chlorine atom, and the other symbols are the same as defined above.]

This reaction is usually carried out in a solvent. Examples of the solvents to be used in the reaction include ethers such as tetrahydrofuran and methyl tert-butyl ether (hereinafter, referred to "ethers"); aromatic hydrocarbons such as toluene and xylene (hereinafter, referred to as "aromatic hydrocarbons"); nitriles; polar aprotic solvents such as N,N-dimethylformamide (hereinafter, referred to as "DMF"), N-methyl pyrrolidone (hereinafter, referred to as "NMP"), and dimethyl sulfoxide (hereinafter, referred to "DMSO") (hereinafter, referred to as "polar aprotic solvent"); and mixed solvents of these two or more solvents.

Examples of the base to be used in the reaction include alkali metal carbonates (such as sodium carbonate, and potassium carbonate) (hereinafter, referred to as "alkali metal carbonates"); and alkali metal hydrides such as sodium hydride (hereinafter, referred to as "alkali metal hydrides").

In the reaction, the compound (R-1) is used usually within a range of 1 to 10 molar ratio(s), and the base is used usually within a range of 1 to 10 molar ratio(s), as opposed to 1 mole of the compound (M-1).

The reaction temperature of the reaction is usually within a range of −20 to 150° C. The reaction period of the reaction is usually within a range of 0.5 to 24 hours.

When the reaction is completed, water is added to reaction mixture, and the reaction mixture are extracted with organic solvent(s), and the organic layers are worked up (for example, drying and concentration) to obtain the compound (I-n0).

The compound (R-1) is a commercially available compound, or can be prepared by using a known method.

Process 3

The present compound N can be prepared by reacting a compound represented by formula (M-3) (hereinafter, referred to as "Compound (M-3)") with a compound represented by formula (M-2) (hereinafter, referred to as "Compound (M-2)") in the presence of a base.

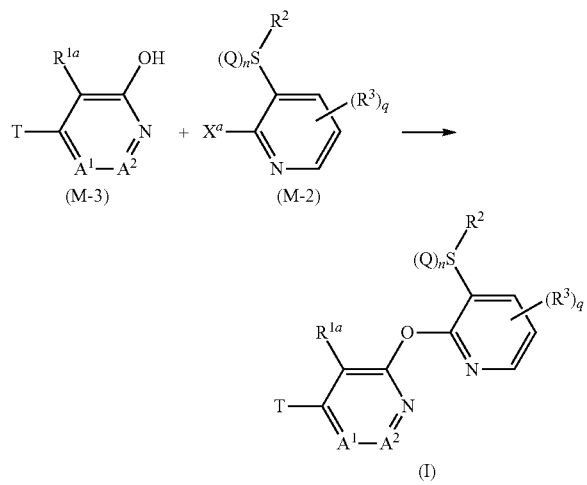

(M-3)  (M-2)

(I)

[wherein, the symbols are the same as defined above.]

The reaction is usually carried out in a solvent. Examples of the solvents to be used in the reaction include ethers, aromatic hydrocarbons, nitriles, and mixed solvents of these two or more solvents.

Examples of the base to be used in the reaction include alkali metal carbonates and alkali metal hydrides.

In the reaction, the compound (M-2) is used usually within a range of 0.8 to 1.2 molar ratios, and the base is used usually within a range of 1 to 10 molar ratio(s), as opposed to 1 mole of the compound (M-3).

The reaction temperature of the reaction is usually within a range of −20 to 150° C. The reaction period of the reaction is usually within a range of 0.5 to 24 hours.

When the reaction is completed, water is added to reaction mixture, and the reaction mixture are extracted with organic solvent(s), and the organic layers are worked up (for example, drying and concentration) to obtain the present compound.

The compound (M-2) is a publically known compound, or may be prepared according to the similar method to that described in Journal of Organic Chemistry, 68(12), 4918, 2003 or WO 2013/086397 A1.

The compound (M-3) is a publically known compound, or may be prepared according to the similar method to that described in WO2005/018557 A1, WO2009/149188 A1, WO2010/104818 A1, or WO2015/153304 A1 and the others.

Process 4

The present compound N can be prepared by reacting a compound represented by formula (M-3) (hereinafter, referred to as "Compound (M-3)") with a compound represented by formula (M-4) (hereinafter, referred to as "Compound (M-4)") in the presence of a metal catalyst and a base.

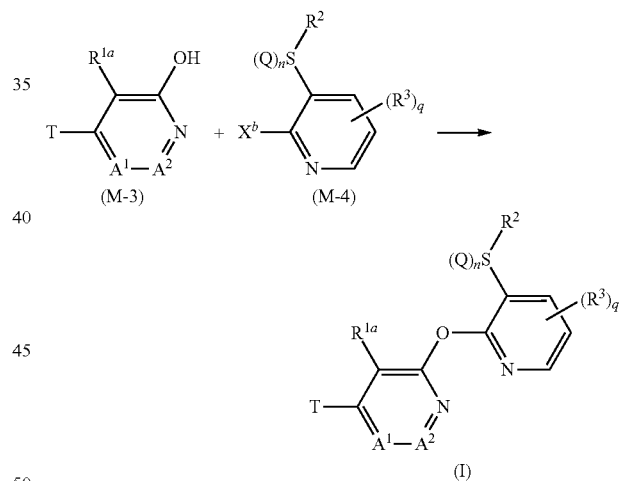

(M-3)  (M-4)

(I)

[wherein, $X^b$ represents a chlorine atom, a bromine atom, or an iodine atom, and the other symbols are the same as defined above.]

The reaction is carried out in a solvent. Examples of the solvent to be used in the reaction include ethers, aromatic hydrocarbons, aprotic polar solvents, water, and mixed solvents of these two or more solvents.

Examples of the metal catalyst to be used in the reaction include copper catalyst such as copper(I) iodide, copper(I) bromide, copper(I) chloride, copper(I) oxide, trifluoromethanesulfonic acid copper(I) salt benzene complex, tetrakis (acetonitrile)copper(I) hexafluorophosphate, and 2-thiophenecarboxylic acid copper(I) salt; and nickel catalyst such as bis (cyclooctadiene)nickel(0) and nickel(II) chloride.

A ligand, a base, or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, 1,10-phenanthroline, trans-1,2-cyclohexanediamine, trans-1,2-bis(methylamino)cyclohexane-1,2-diamine, and N,N'-dimethylethylenediamine.

Examples of the base to be used in the reaction include organic bases such as triethylamine, diisopropylethylamine, pyridine, and 4-(dimethylamino)pyridine (hereinafter, referred to as "organic bases"); alkali metal hydrides; and alkali metal carbonates.

Examples of the inorganic halogenated compounds to be used in the reaction include alkali metal fluorides such as potassium fluoride, and sodium fluoride; and alkali metal chlorides such as lithium chloride and sodium chloride.

In the reaction, the compound (M-4) is usually used within a range of 0.8 to 1.2 molar ratios, the metal catalyst is usually used within a range of 0.01 to 2 molar ratios, as opposed to 1 mole of the compound (M-3). When the ligand, the base or the inorganic halogenated compound is used in the reaction, the ligand is usually used within a range of 0.01 to 1 molar ratio(s), the base is usually used within a range of 0.1 to 5 molar ratios, and the inorganic halogenated compound is usually used within a range of 0.1 to 5 molar ratios, as opposed to 1 mole of the compound (M-3).

The reaction temperature is usually within a range of −20 to 200° C. The reaction period of the reaction is usually within a range of 0.1 to 24 hours.

When the reaction is completed, water is added to reaction mixture, and the reaction mixture are extracted with organic solvent(s), and the organic layers are worked up (for example, drying and concentration) to obtain the present compound.

The compound (M-4) is a publically known compound, or may be prepared according to the similar method to that described in Synthesis, 45(11), 1489, 2013, or WO 2012/122011 and so on.

Process 5

A compound represented by formula (I-Ta) (hereinafter, referred to as "Compound (I-Ta)") can be prepared by reacting a compound represented by formula (M-5) (hereinafter, referred to as "Compound (M-5)") with a compound represented by formula (R-2) (hereinafter, referred to as "Compound (R-2)") in the presence of a base.

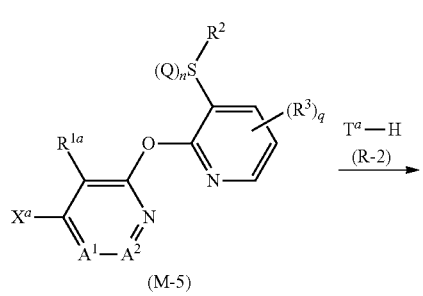

(M-5)

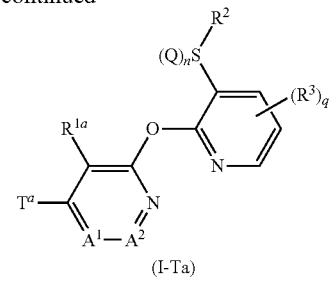

(I-Ta)

[wherein, $T^a$ represents $OR^6$, $SR^6$, $NR^6R^7$, or a group represented by formula $T^3$, and the other symbols are the same as defined above.]

The reaction is usually conducted in a solvent. Examples of the solvents to be used in the reaction include ethers, aromatic hydrocarbons, nitriles, aprotic polar solvents, and mixed solvents of these two or more solvents.

Examples of the base to be used in the reaction include alkali metal carbonates and alkali metal hydrides.

In the reaction, the compound (R-2) is used usually within a range of 0.8 to 1.2 molar ratios, and the base is used usually within a range of 1 to 10 molar ration(s), as opposed to 1 mole of the compound (M-5).

The reaction temperature is usually within a range of −20 to 150° C. The reaction period of the reaction is usually within a range of 0.5 to 24 hours.

When the reaction is completed, to the reaction mixture is added water, and the reaction mixture are extracted with organic solvent(s), and the organic layers are worked up (for example, drying and concentration) to obtain the compound (I-Ta).

The compound (R-2) is a commercially available compound, or can be prepared by using a known method.

Process 6

A compound represented by formula (I-Tb) (hereinafter, referred to as "Compound (I-Tb)") can be prepared by reacting a compound represented by formula (M-6) (hereinafter, referred to as "Compound (M-6)") with a compound represented by formula (R-3) (hereinafter, referred to as "Compound (R-3)") in the presence of a metal catalyst.

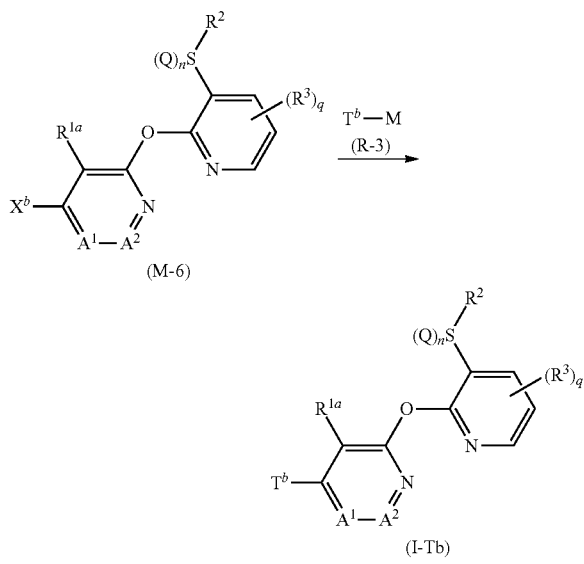

[wherein, T^b represents a group represented by formula T^1 or a group represented by formula T^2, and M represents a 9-borabicyclo[3.3.1]nonan-9-yl group, a borono group, a 4,4,5,5,-tetramethyl-1,3,2-dioxaborolan-2-yl, a tributylstannyl group, ZnCl, MgCl, or MgBr, and the other symbols are the same as defined above.]

The reaction is usually carried out in a solvent. Examples of the solvents to be used in the reaction include ethers, aromatic hydrocarbons, polar aprotic solvents, water, and mixed solvents of these two or more solvents.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

A ligand, a base, or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

The bases to be used in the reaction include alkali metal hydrides, alkali metal carbonates, and organic bases.

Examples of the inorganic halogenated compounds include alkali metal fluorides such as potassium fluorides and sodium fluorides; and alkali metal chlorides such as lithium chloride and sodium chloride.

In the reaction, the compound (R-3) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratios, and the inorganic halogenated compound is usually used within a range of 0.1 to 5 molar ratios, as opposed to 1 mole of the compound (M-6).

The reaction temperature of the reaction is usually within a range of −20 to 200° C. The reaction period of the reaction is usually within a range of 0.1 to 24 hours.

When the reaction is completed, water is added to the reaction mixture, and the reaction mixture are extracted with organic solvent(s), and the organic solvents are worked up (for example, drying and concentration) to obtain the compound (I-Tb).

The compound (R-3) is a publically known compound, or can be prepared according to the publically known method.

Process 7

A compound represented by formula (I-TOR6) (hereinafter, referred to as "Compound (I-TROR6)") can be prepared by reacting a compound represented by formula (M-7) (hereinafter, referred to as "Compound (M-7)") with a compound represented by formula (R-4) (hereinafter, referred to as "Compound (R-4)") in the presence of a base.

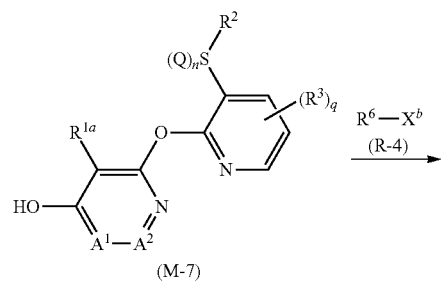

(M-7)

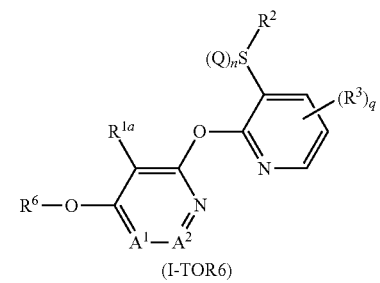

(I-TOR6)

[wherein, the symbols are the same as defined above.]

The reaction can be carried out by using the compound (M-7) instead of the compound (R-2) and the compound (R-4) instead of the compound (M-5), according to the method described in the process 5.

The compound (R-4) is a commercially available compound, or can be prepared by using a known method.

Process 8

A compound represented by formula (I-n1QN) (hereinafter, referred to as "Compound (I-n1QN)") and a compound represented by formula (I-n2QN) (hereinafter, referred to as "Compound (I-n2QN)") can be prepared according to the following scheme.

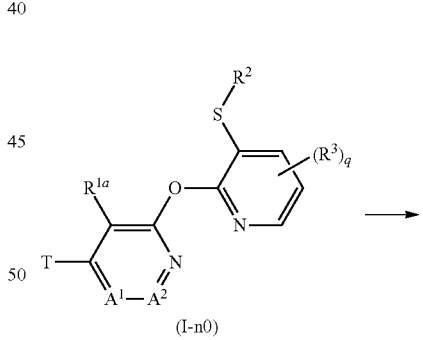

(I-n0)

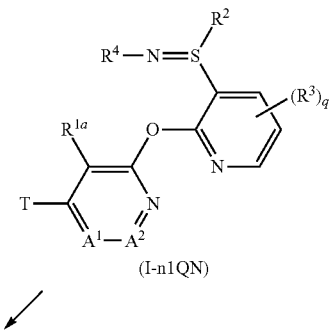

(I-n1QN)

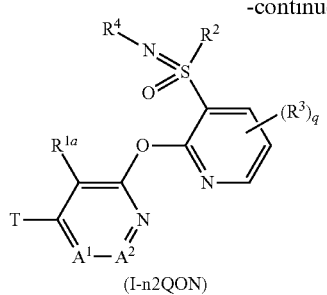

(I-n2QON)

[wherein, the symbols are the same as defined above.]

The compound (I-n1QN) can be prepared by using the compound (I-n0) according to the method described in Organic Letters, 9(19), 3809, 2007.

The compound (I-n2QON) can be prepared by using the compound (I-n1QN) according to the method for preparing the compound (I-n1QO) from the compound (I-n0) as described in the process 1.

Process 9

A compound represented by formula (I-n2QO-NO) can be prepared by reacting the compound (I-n2QO) with an oxidizing agent.

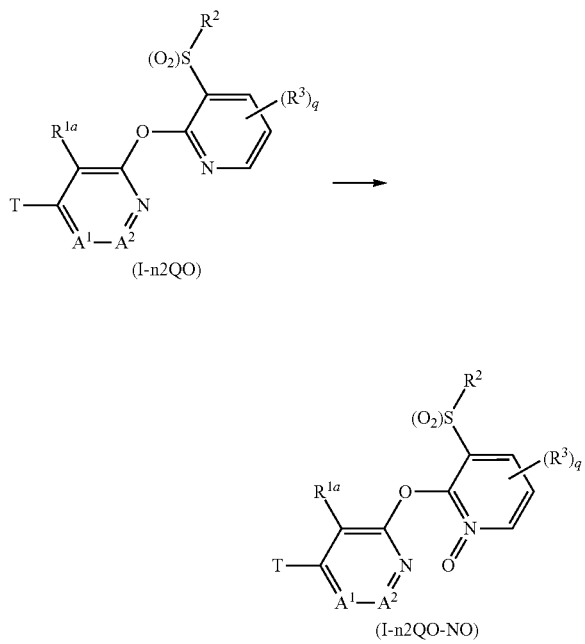

[wherein, the symbols are the same as defined above.]

The reaction can be carried out according to the methods described in the process 1, US patent publication No. 2018/0009776 A1, or WO 2016/121970 A1.

Hereinafter, a process for preparing a production intermediate compound is described.

Reference Process 1

The compound (M-1) can be prepared by reacting the compound (M-3) with a compound represented by formula (M-8) (hereinafter, referred to as "Compound (M-8)") in the presence of a base.

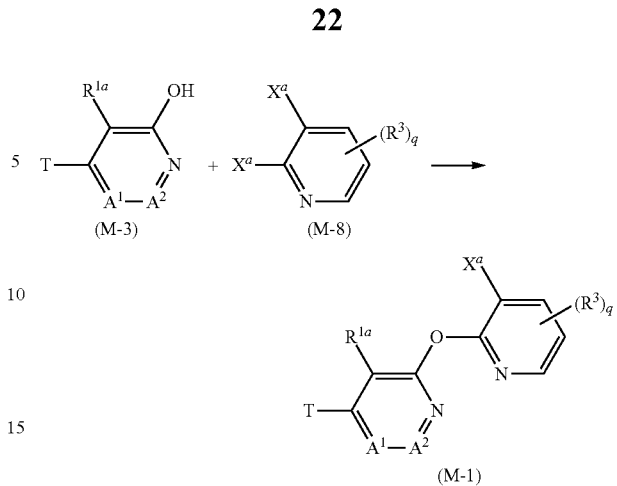

[wherein, the symbols are the same as defined above.]

The reaction can be carried out by using the compound (M-8) according to the process 3.

The compound (M-8) is a publically known compound, or can be prepared according to the method described in WO 2015/187845 A1.

Reference Process 2

A compound represented by formula (M-10) (hereinafter, referred to as "Compound (M-10)") can be prepared by reacting a compound represented by formula (M-9) (hereinafter, referred to as "Compound (M-9)") with the compound (M-4) in the presence of a base.

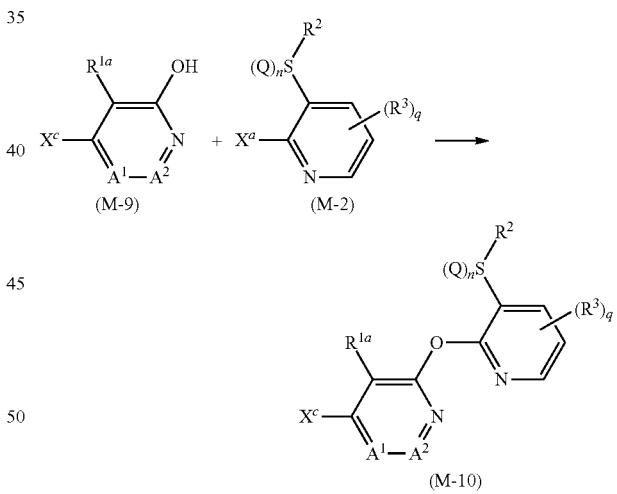

[wherein, $X^c$ represents a halogen atom, and the other symbols are the same as defined above.]

The reaction can be carried out by using the compound (M-9) instead of the compound (M-3) according to the process 3.

The compound (M-9) is a publically known compound, or can be prepared according to the method described in Synlett, 27 (1), 67, 2016.

Reference Process 3

The compound (M-7) can be prepared according to the following scheme.

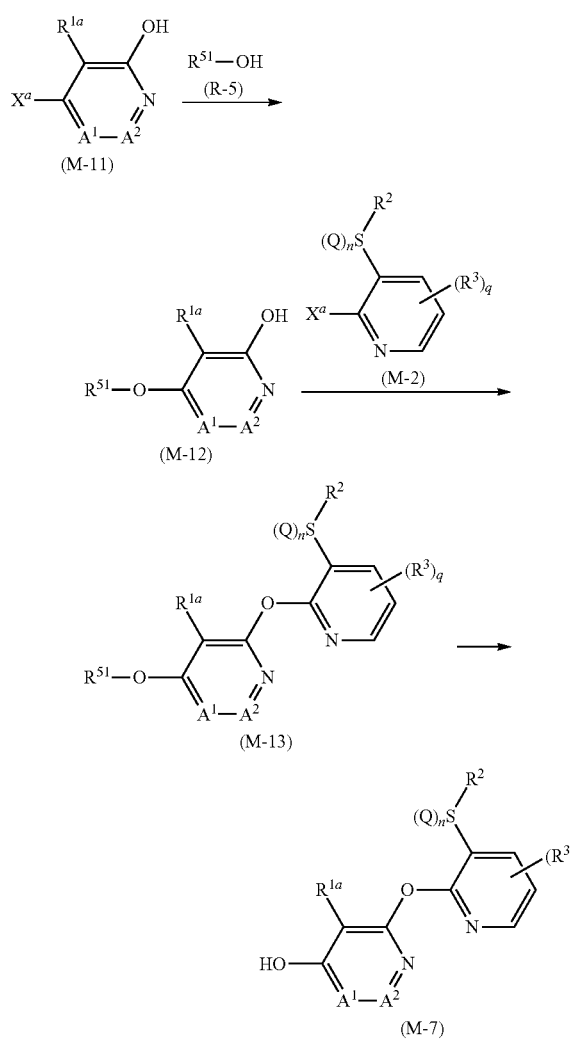

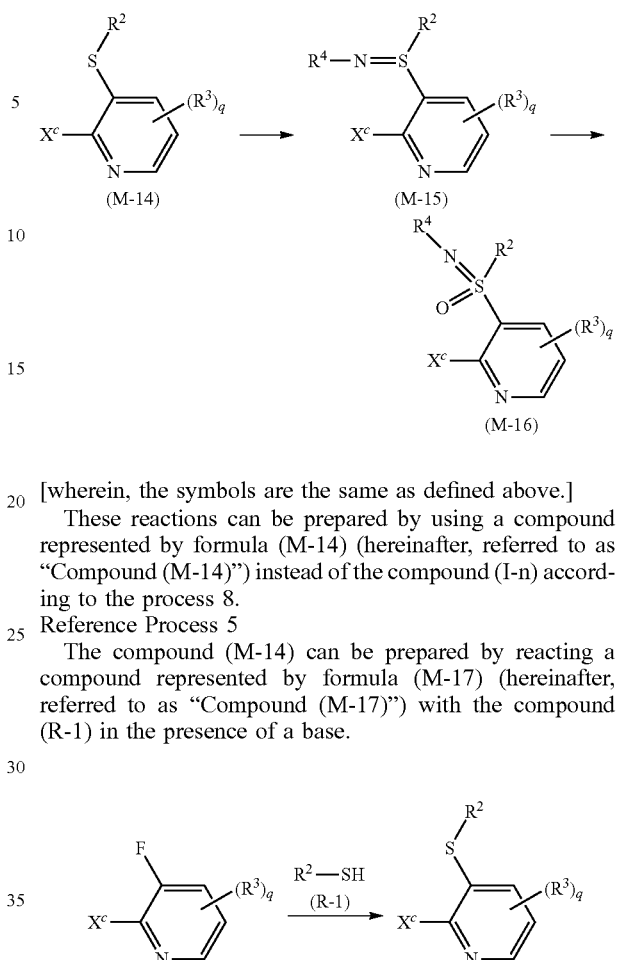

[wherein, the symbols are the same as defined above.]

These reactions can be prepared by using a compound represented by formula (M-14) (hereinafter, referred to as "Compound (M-14)") instead of the compound (I-n) according to the process 8.

Reference Process 5

The compound (M-14) can be prepared by reacting a compound represented by formula (M-17) (hereinafter, referred to as "Compound (M-17)") with the compound (R-1) in the presence of a base.

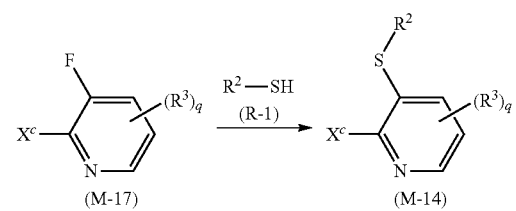

[wherein, the symbols are the same as defined above.]

The reaction can be carried out by using the compound (M-17) instead of the compound (M-1) according to the process 2.

Reference Process 6

A compound represented by formula (M-18) or a compound represented by formula (M-19) can be prepared by oxidizing the compound (M-14).

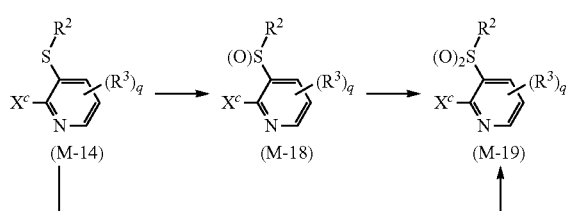

[wherein, the symbols are the same as defined above.]

These reactions can be carried out by using the compound (M-14) instead of the compound (I-n0) according to the process 1.

Reference Process 7

A compound represented by formula (M-21) can be prepared by using a compound represented by formula (M-20) (hereinafter, referred to as "Compound (M-20)")

[wherein, $R^{51}$ represents a methyl group or an ethyl group, and the other symbols are the same as defined above.]

A compound represented by formula (M-12) (hereinafter, referred to as "Compound (M-12)") can be prepared by reacting a compound represented by formula (M-11) (hereinafter, referred to as "Compound (M-11)") with a compound represented by formula (R-5) (hereinafter, referred to as "Compound (R-5)"), according to the process 5.

A compound represented by formula (M-13) (hereinafter, referred to as "Compound (M-13)") can be prepared by reacting the compound (M-12) with the compound (M-2) according to the process 3.

The compound (M-7) can be prepared by reacting the compound (M-13) with an acid. The reaction can be carried out according to the method described in, for example, WO 2016/052455 A1.

The compound (M-11) is a commercially available compound, or can be prepared by using a known method.

Reference Process 4

A compound represented by formula (M-15) and a compound represented by formula (M-16) can be prepared according to the following scheme.

with a compound represented by formula (R-6) (hereinafter, referred to as "Compound (R-6)") in the presence of a metal catalyst,

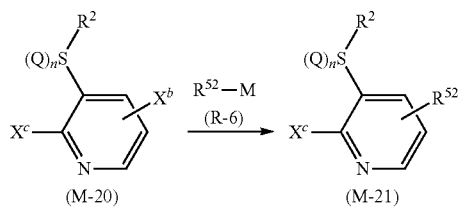

[wherein, $R^{52}$ represents a C1-C6 chain hydrocarbon group which may be optionally one or more substituents selected from Group A, a C3-C7 cycloalkyl group which may be optionally one or more substituents selected from Group B, a phenyl group which may be optionally one or more substituents selected from Group C, or a five or six membered aromatic heterocyclic group which may be optionally substituted with one or more substituents selected from Group C, and the other symbols are the same as defined above.]

The reaction can be carried out by using the compound (M-20) instead of the compound (M-6) and the compound (R-6) instead of the compound (R-3), according to the process 6.

The compound (R-6) is a commercially available compound, or can be prepared by using a known method.

Reference Process 8

A compound represented by formula (M-23) can be prepared by reacting a compound represented by formula (M-22) (hereinafter, referred to as "Compound (M-22)") with a compound represented by formula (R-7) (hereinafter, referred to as "Compound (R-7)) in the presence of a base.

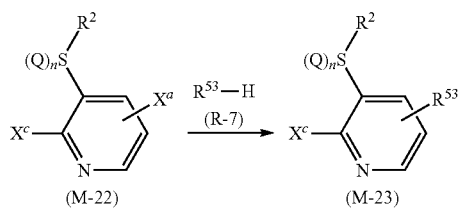

[wherein, $R^{53}$ represents $OR^8$, $NR^7R^8$, $NR^7R^8R^9$ or $NR^7OR^9$, and the other symbols are the same as defined above.]

The reaction can be carried out by using the compound (M-22) instead of the compound (M-5) and the compound (R-7 instead of the compound (R-2), according to the process 5.

The compound (R-7) is a commercially available compound, or can be prepared by using a known method.

The compound of the present invention may be mixed or combined with one or more kinds of ingredients selected from a group consisting of the following Group (a), Group (b), Group (c), and Group (d) (hereinafter, referred to as "Present ingredient").

The above-mentioned mixing or combining represents a use of the Present compound and the Present ingredient at same time, separately or at certain intervals.

When the Present compound and the present ingredient are used at the same time, the Present compound and the Present ingredient may be contained in separate formulations respectively or may be contained in the same one formulation.

One aspect of the present invention is a composition comprising one or more ingredients selected from Group (a), Group (b), Group (c), and Group (d) as well as the Present compound (hereinafter, referred to as "Composition A").

Group (a) is a group consisting of
each active ingredient as Acetylcholinesterase inhibitors (for example, carbamate insecticides, or organophosphorus insecticides), GABA-gated chloride channel blockers (for example, phenylpyrazol insecticides), Sodium channel modulators (for example, pyrethroid insecticides), Nicotinic acetylcholine receptor competitive modulators (for example, neonicotinoid insecticides), Nicotinic acetylcholine receptor allosteric modulators, Glutamatergic chlorine ion channel allosteric modulators (for example, macrolide insecticides), Juvenile hormone mimic, Multisite inhibitors, chordotonal organ TRPV channel modulators, Mites growth inhibitors, Mitochondria ATP biosynthetic enzyme inhibitors, Uncouplers of oxidative phosphorylation, Nicotinic acetylcholine receptor channel blocker (for example, Nereistoxin insecticides), Chitin synthesis inhibitors, Molting inhibitors, Ecdysone receptor agonist, Octopamine receptor agonist, Inhibitors of Mitochondrial electron transport system complex I, II, III and IV, Voltage-dependent sodium channel blockers, Acetyl CoA carboxylase inhibitor, Ryanodine receptor modulator (for example, Diamide insecticides), Chordotonal organ modulators, Microbial pesticides; and
the other insecticidal, miticidal or nematicidal active ingredients.

These ingredients are classified as a class based on the action mechanism of IRAC.

Group (b) is a group consisting of
Nucleic acid synthesis inhibitors (for example, Phenylamide fungicides, or Acylamino acid fungicides), cell division and cytoskeleton inhibitors (for example, MBC fungicides), Respiratory inhibitors (for example, QoI fungicides or QiI fungicides), Amino acid synthesis and protein synthesis inhibitors (for example, anilinopyridine fungicides), Signal transduction inhibitors, Lipid synthesis and membrane synthesis inhibitors, sterol biosynthesis inhibitors (for example, DMI fungicides such as triazole), cell wall synthesis inhibitors, Melanin synthesis inhibitors, Plant defense inducers, Other action point contact active fungicides, Microbial fungicides, and the other fungicidal ingredients. These are classified as a class based on the action mechanism of FRAC.

Group (c) is a plant growth modulating ingredient group (including Mycorrhizal fungi, and Root nodule bacteria).

Group (d) is a repellent component.

Examples of the combination of the Present ingredient and the Present compound are described below. For example, alanycarb+SX represents a combination of alanycarb and SX.

The symbol of "SX" represents any one of the Present compound selected from the Compound Class $SX_1$ to the Compound Class $SX_{80}$. Also, all of the below-mentioned present active ingredient are known ingredients, and are commercially available or may be produced by the known method. If the present ingredient is a bacterium, it is available from the bacterial authority depository. The numerical number in bracket represents a CAS RN (Register Trademark).

Combination of the Present ingredient of the above Group (a) and the Present compound:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC (2-methyl-4,6-dinitrophenol)+SX, doramectin+SX, dried leaves of Dryopteris filix-mas+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*)+SX, extract of *Cassia nigricans*)+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hv1a peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthri+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides*+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo- 6-chloro-4-(1,1,1,2,3,3,3-heptafluoropropan-2-yl) phenyl]-3-[ethyl(4-cyanobenzoyl)amino]-2-methoxybenzamide (1609007-65-9)+SX, N-[2-bromo-6-(difluoromethoxy)-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfanyl]phenyl}-3-(trifluoromethyl)-1H-1,2,4-triazol-5-amine (885026-50-6)+SX, BT crop protein Cry1Ab+SX, BT crop protein Cry1Ac+SX, BT crop protein Cry1Fa+SX, BT crop protein Cry1A105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, Adoxophyes orana granulosis virus strain BV-0001+SX, Anticarsia gemmatalis mNPV+SX, Autographa californica mNPV+SX, Cydia pomonella GV strain V15+SX, Cydia pomonella GV strain V22+SX, Cryptophlebia leucotreta GV+SX, Dendrolimus punctatus cypovirus+SX, Helicoverpa armigera NPV strain BV-0003+SX, Helicoverpa zea NPV+SX, Lymantria dispar NPV+SX, Mamestra brassicae NPV+SX, Mamestra configurata NPV+SX, Neodiprion abietis NPV+SX, Neodiprion lecontei NPV+SX, Neodiprion sertifer NPV+SX, Nosema locustae+SX, Orgyia pseudotsugata NPV+SX, Pieris rapae GV+SX, Plodia interpunctella GV+SX, Spodoptera exigua mNPV+SX, Spodoptera littoralis mNPV+SX, Spodoptera litura NPV+SX, Arthrobotrys dactyloides+SX, Bacillus firmus strain GB-126+SX, Bacillus firmus strain I-1582+SX, Bacillus megaterium+SX, Bacillus sp. strain AQ175+SX, Bacillus sp. strain AQ177+SX, Bacillus sp. strain AQ178+SX, Bacillus sphaericus strain 2362+SX, Bacillus sphaericus strain ABTS1743+SX, Bacillus sphaericus Serotype strain H5a5b+SX, Bacillus thuringiensis strain AQ52+SX, Bacillus thuringiensis strain BD #32+SX, Bacillus thuringiensis strain CR-371+SX, Bacillus thuringiensis subsp. Aizawai strain ABTS-1857+SX, Bacillus thuringiensis subsp. Aizawai strain AM65-52+SX, Bacillus thuringiensis subsp. Aizawai strain GC-91+SX, Bacillus thuringiensis subsp. Aizawai Serotype strain H-7+SX, Bacillus thuringiensis subsp. Kurstaki strain ABTS351+SX, Bacillus thuringiensis subsp. Kurstaki strain BMP123+SX, Bacillus thuringiensis subsp. Kurstaki strain EG234+SX, Bacillus thuringiensis subsp. Kurstaki strain EG7841+SX, Bacillus thuringiensis subsp. Kurstaki strain EVB113-19+SX, Bacillus thuringiensis subsp. Kurstaki strain F810+SX, Bacillus thuringiensis subsp. Kurstaki strain HD-1+SX, Bacillus thuringiensis subsp. Kurstaki strain PB54+SX, Bacillus thuringiensis subsp. Kurstaki strain SA11+SX, Bacillus thuringiensis subsp. Kurstaki strain SA12+SX, Bacillus thuringiensis subsp. Tenebriosis strain NB176+SX, Bacillus thuringiensis subsp. Thuringiensis strain MPPL002+SX, Bacillus thuringiensis subsp. morrisoni+SX, Bacillus thuringiensis var. colmeri+SX, Bacillus thuringiensis var. darmstadiensis strain 24-91+SX, Bacillus thuringiensis var. dendrolimus+SX, Bacillus thuringiensis var. galleriae+SX, Bacillus thuringiensis var. israelensis strain BMP144+SX, Bacillus thuringiensis var. israelensis serotype strain H-14+SX, Bacillus thuringiensis var. japonensis strain buibui+SX, Bacillus thuringiensis var. san diego strain M-7+SX, Bacillus thuringiensis var. 7216+SX, Bacillus thuringiensis var. aegypti+SX, Bacillus thuringiensis var. T36+SX, Beauveria bassiana strain ANT-03+SX, Beauveria bassiana strain ATCC74040+SX, Beauveria bassiana strain GHA+SX, Beauveria brongniartii+SX, Burkholderia rinojensis strain A396+SX, Chromobacterium subtsugae strain PRAA4-1T+SX, Dactyllela ellipsospora+SX, Dectylaria thaumasia+SX, Hirsutella minnesotensis+SX, Hirsutella rhossiliensis+SX, Hirsutella thompsonii+SX, Lagenidium giganteum+SX, Lecanicillium lecanii strain KV01+SX, Lecanicillium lecanii conidia of strain DAOM198499+SX, Lecanicillium lecanii conidia of strain DAOM216596+SX, Lecanicillium muscarium strain Ve6+SX, Metarhizium anisopliae strain F52+SX, Metarhizium anisopliae var. acridum+SX, Metarhizium anisopliae var. anisopliae BIPESCO 5/F52+SX, Metarhizium flavoviride+SX, Monacrosporium phymatopagum+SX, Paecilomyces fumosoroseus Apopka strain 97+SX, Paecilomyces lilacinus strain 251+SX, Paecilomyces tenuipes strain T1+SX, Paenibacillus popilliae+SX, Pasteuria nishizawae strain Pn1+SX, Pasteuria penetrans+SX, Pasteuria usgae+SX, Pasteuria thoynei+SX, Serratia entomophila+SX, Verticillium chlamydosporium+SX, Verticillium lecani strain NCIM1312+SX, 2-chloro-4-fluoro-5-{[5-(trifluoromethylthio)pentyl]oxy}phenyl 2,2,2-trifluoroethyl sulfoxide (1472050-04-6)+SX, 4-chloro-5-[2,2-difluoro-2-(3,4,5-trifluorophenyl)ethoxy]-2-methylphenyl 2,2,2-trifluoroethyl sulfoxide (1632218-00-8)+SX, 4-fluoro-5-[2,2-difluoro-2-(3,4,5-trifluorophenyl)ethoxy]-2-methylphenyl 2,2,2-trifluoroethyl sulfoxide (1632217-98-1)+SX, 2-({2-fluoro-4-methyl-5-[(2,2,2-trifluoroethyl)sulfinyl]phenyl}imino)-3-(2,2,2-trifluoroethyl)-1,3-thiazolidin-4-one (1445683-71-5)+SX, (1Z)-2-(4-tert-butylphenyl)-2-cyano-1-(1-ethyl-3-methyl-1H-pyrazol-5-yl)ethenyl 2,2-dimethylpropanoate (1253429-01-4)+SX, N-[(1S,2S)-2-(2,4-dichlorophenyl)cyclobutyl]-2-(trifluoromethyl)pyridine-3-carboxamide (1644251-74-0)+SX, (3R)-3-(2-chlorothiazol-5-yl)-8-methyl-7-oxo-6-phenyl-2,3-dihydrothiazolo[3,2-a]pyrimidin-4-ium-5-olate (2249718-27-0)+SX.

Combination of the Present ingredient of the above Group (b) and the Present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthiavalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+

SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxapiprolin+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin}+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph)+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]pyrimidin-4-amine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R,2S,5S)-5-(4-chlorobenzyl)-2-(chloromethyl)-2-methyl-1-(1H-1,2,4-triazol-1-ylmethyl)cyclopentan-1-ol (1801930-06-2)+SX, (1S,2R,5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R,2S,5S)-2-(chloromethyl)-5-(4-fluorobenzyl)-2-methyl-1-(1H-1,2,4-triazol-1-ylmethyl)cyclopentan-1-ol (1801930-08-4)+SX, (1S,2R,5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Agrobacterium* radiobacter strain K1026+SX, *Agrobacterium* radiobacter strain K84+SX, *Bacillus amyloliquefaciens* (Aveo™ EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX,

*Bacillus amyloliquefaciens* strain MBI600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB-2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain O+SX, *Candida saitoana*+SX, *Chaetomium cupreum*+SX, *Clonostachys rosea*+SX, *Coniothyrium minitans* strain CGMCC8325+SX, *Coniothyrium minitans* strain CON/M/91-8+SX, *Cryptococcus albidus*+SX, *Erwinia carotovora* subsp. *carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, *Pseudozyma flocculosa* strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma asperellum* strain ICC012+SX, *Trichoderma asperellum* SKT-1+SX, *Trichoderma asperellum* strain T25+SX, *Trichoderma asperellum* strain T34+SX, *Trichoderma asperellum* strain TV1+SX, *Trichoderma atroviride* strain CNCM 1-1237+SX, *Trichoderma atroviride* strain LC52+SX, *Trichoderma atroviride* strain IMI 206040+SX, *Trichoderma atroviride* strain SC1+SX, *Trichoderma atroviride* strain SKT-1+SX, *Trichoderma atroviride* strain T11+SX, *Trichoderma gamsii* strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain MO1+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI206039+SX, *Trichoderma stromaticum*+SX, *Trichoderma virens* strain G-41+SX, *Trichoderma virens* strain GL-21+SX, *Trichoderma viride*+SX, *Variovorax paradoxus* strain CGF4526+SX, Harpin protein+SX, N'-[5-choro-4-(2-fluorophenoxy)-2-methylphenyl)-N-ethyl-N-methylmethanimidamide (2055589-28-9)+SX, N'-[2-choro-4-(2-fluorophenoxy)-5-methylphenyl)-N-ethyl-N-methylmethanimidamide (2055756-21-1)+SX, N'-[4-(1-hydroxy-1-phenyl-2,2,2-trifluoroethyl)-2-methyl-5-methoxyphenyl)-N-isopropyl-N-methylmethanimidamide (2101814-55-3)+SX, N'-[5-bromo-6-(1-methyl-2-propoxyethoxy)-2-methylpyridin-3-yl)-N-ethyl-N-methylmethanimidamide (1817828-69-5)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 4-({6-[2-(2,4-difluorophenyl)-1,1-difluoro-2-hydroxy-3-(1H-1,2,4-triazol-1-yl)propyl]pyridin-3-yl}oxy)benzonitrile (2046300-61-0)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)propan-2-ol (2082660-27-1)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl}amino)-6-methylpyrimidine (1605340-92-8)+SX, N-(1-benzyl-1,3-dimethylbutyl)-8-fluoroquinoline-3-carboxamide (2132414-04-9), N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl]phenyl}methyl)isoxazolidin-3-one (2098918-25-1)+SX, 5,5-dimethyl-2-({4-[5-(trifluoromethyl)-1,2,4-oxadiazol-3-yl]phenyl}methyl)isoxazolidin-3-one (2098918-26-2)+SX.

Combination of the Present ingredient of the above Group (c) and the Present compound:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy) acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+

SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, 5-(trifluoromethyl)benz[b]thiophene-2-carboxylic acid methyl+SX, 3-[(6-chloro-4-phenylquinazolin-2-yl) amino]-1-propanol+SX, Claroideoglomus etunicatum+SX, Claroideoglomus claroideum+SX, Funneliformis mosseae+SX, Gigaspora margarita+SX, Gigaspora rosea+SX, Glomus aggregatum+SX, Glomus deserticola+SX, Glomus monosporum+SX, Paraglomus brasillianum+SX, Rhizophagus clarus+SX, Rhizophagus intraradices RTI-801+SX, Rhizophagus irregularis DAOM 197198+SX, Azorhizobium caulinodans+SX, Azospirillum amazonense+SX, Azospirillum brasilense XOH+SX, Azospirillum brasilense Ab-V5+SX, Azospirillum brasilense Ab-V6+SX, Azospirillum caulinodans+SX, Azospirillum halopraeferens+SX, Azospirillum irakense+SX, Azospirillum lipoferum+SX, Bradyrhizobium elkanii SEMIA 587+SX, Bradyrhizobium elkanii SEMIA 5019+SX, Bradyrhizobium japonicum TA11+SX, Bradyrhizobium japonicum USDA110+SX, Bradyrhizobium liaoningense+SX, Bradyrhizobium lupini+SX, Delftia acidovorans RAY209+SX, Mesorhizobium ciceri+SX, Mesorhizobium huakii+SX, Mesorhizobium loti+SX, Rhizobium etli+SX, Rhizobium galegae+SX, Rhizobium leguminosarum bv. Phaseoli+SX, Rhizobium leguminosarum bv. Trifolii+SX, Rhizobium leguminosarum bv. Viciae+SX, Rhizobium trifolii+SX, Rhizobium tropici+SX, Sinorhizobium fredii+SX, Sinorhizobium meliloti+SX, Zucchini Yellow Mosaik Virus weak strain+SX.

Combination of the Present ingredient of the above Group (d) and the Present compound:

anthraquinone+SX, deet+SX, icaridin+SX.

The ratio of the Present compound to the Present ingredient includes, but not limited thereto, as a ratio by weight (the Present compound:the Present ingredient) 1,000:1 to 1:1,000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:50, and the others.

The present compound has control effect on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), *Tagosodes orizicolus*, and the like;

from the family Cicadellidae, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and the like;

from the family Cercopidae, *Mahanarva posticata, Mahanarva fimbriolata*, and the like;

from the family Aphididae, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and the like;

from the family Phylloxeridae, grapevine phylloxera (*Daktulosphaira vitifoliae*), Pecan phylloxera (*Phylloxera devastatrix*), Pecan leaf phylloxera (*Phylloxera notabilis*), Southern pecan leaf phylloxera (*Phylloxera russellae*), and the like;

from the family Adelgidae, hemlock woolly aphid (*Adelges tsugae*), *Adelges piceae, Aphrastasia pectinatae*, and the like;

from the family Pentatomidae, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax, Dichelops melacanthus*, and the like;

from the family Cydnidae, Burrower brown bug (*Scaptocoris castanea*);

from the family Alydidae, for example, bean bug (*Riptortus pedestris*), corbett rice bug (*Leptocorisa chinensis*), rice bug (*Leptocorisa acuta*), and the like;

from the family Coreidae, *Cletus punctiger*, Australian leaf-footed bug (*Leptoglossus australis*), and the like;

from the family Lygaeidae, oriental chinch bug (*Caverelius saccharivorus*), seed bug (*Togo hemipterus*), chinch bug (*Blissus leucopterus*), and the like;

from the family Miridae, rice leaf bug (*Trigonotylus caelestialium*), sorghum plant bug (*Stenotus rubrovittatus*), wheat leaf bug (*Stenodema calcarata*), American tarnished plant bug (*Lygus lineolaris*), and the like;

from the family Aleyrodidae, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), *Pealius euryae*, and the like;

from the family Diaspididae, *Abgrallaspis cyanophylli*, red scale (*Aonidiella aurantii*), San Jose scale (*Diaspidiotus perniciosus*), white peach scale (*Pseudaulacaspis pentagona*), arrowhead scale (*Unaspis yanonensis*), citrus snow scale (*Unaspis citri*), and the like;

from the family Coccidae, pink wax scale (*Ceroplastes rubens*);

from the family Margarodidae, fluted scale (*Icerya purchasi*) seychelles fluted scale (*Icerya seychellarum*), and the like;

from the family Pseudococcidae, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), tuttle mealybug (*Brevennia rehi*), and the like;

from the family Psyllidae, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), Pear psylla (*Cacopsylla pyricola*), and the like;

from the family Tingidae, sycamore lace bug (*Corythucha ciliata*), aster tingid (*Corythucha marmorata*), Japanese pear lace bug (*Stephanitis nashi*), azalea lace bug (*Stephanitis pyrioides*), and the like;

from the family Cimicidae, common bed bug (*Cimex lectularius*), tropical bed bug (*Cimex lectularius*), and the like;

from the family Cicadidae, Giant Cicada (*Quesada gigas*), and the like;

from the family Reduviidae, *Triatoma infestans*, *Rhodonius prolixus*, and the like, *Triatoma* spp.

Lepidoptera:

from the family Crambidae, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), Sugarcane borer (*Diatraea saccharalis*), and the like;

from the family Pyralidae, lesser cornstalk borer (*Elasmopalpus lignosellus*), mealworm moth (*Plodia interpunctella*), persimmon bark borer (*Euzophera batangensis*), fig moth (*Cadra cautella*), and the like;

from the family Noctuidae, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), Velvetbean caterpillar (*Anticarsia gemmatalis*), Cotton leafworm (*Alabama argillacea*), Hop vine borer (*Hydraecia immanis*), and the like;

from the family Pieridae, common cabbage worm (*Pieris rapae*), and the like;

from the family Tortricidae, oriental fruit moth (*Grapholita molesta*), *Grapholita dimorpha*, soybean moth (*Leguminivora glycinivorella*), *Matsumuraeses azukivora*, summer fruit tortrix (*Adoxophyes orana fasciata*), smaller tea tortrix (*Adoxophyes honmai*), Japanese tea tortrix (*Homona magnanima*), apple tortrix (*Archips fuscocupreanus*), codling moth (*Cydia pomonella*), sugarcane shoot borer (*Tetramoera schistaceana*), Bean Shoot Borer (*Epinotia aporema*), Citrus fruit borer (*Ecdytolopha aurantiana*), and the like;

from the family Gracillariidae, tea leaf roller (*Caloptilia theivora*), Asiatic apple leaf miner (*Phyllonorycter ringoniella*), and the like;

from the family Carposinidae, peach fruit moth (*Carposina sasakii*), and the like;

from the family Lyonetiidae, Coffee Leaf miner (*Leucoptera coffeella*), peach leaf miner (*Lyonetia clerkella*), *Lyonetia prunifoliella*, and the like;

from the family Lymantriidae, *Lymantria* spp. (such as gypsy moth (*Lymantria dispar*)), *Euproctis* spp. (such as tea lymantriid (*Euproctis pseudoconspersa*)), and the like;

from the family Plutellidae, diamondback moth (*Plutella xylostella*), and the like;

from the family Gelechiidae, peach worm (*Anarsia lineatella*), sweetpotato leaf folder (*Helcystogramma triannulella*), pink bollworm (*Pectinophora gossypiella*), potato moth (*Phthorimaea operculella*), *Tuta absoluta*, and the like;

from the family Arctiidae, American white moth (*Hyphantria cunea*), and the like;

from the family Castniidae, Giant Sugarcane borer (*Telchin licus*), and the like;

from the family Cossidae, *Cossus insularis*, and the like;

from the family Geometridae, *Ascotis selenaria*, and the like;

from the family Limacodidae, blue-striped nettle grub (*Parasa lepida*), and the like;

from the family Stathmopodidae, persimmon fruit moth (*Stathmopoda masinissa*), and the like;

from the family Sphingidae, tobacco hornworm (*Acherontia lachesis*), and the like;

from the family Sesiidae, *Nokona feralis*, cherry borer (*Synanthedon hector*), *Synanthedon tenuis*, and the like;

from the family Hesperiidae, rice skipper (*Parnara guttata*), and the like;

from the family Tineidae, casemaking clothes moth (*Tinea translucens*), common clothes moth (*Tineola bisselliella*), and the like.

Thysanoptera:

from the family Thripidae, western flower thrips (*Frankliniella occidentalis*), oriental thrips (*Thrips palmi*) yellow tea thrips (*Scirtothrips dorsalis*), onion thrips (*Thrips tabaci*), eastern flower thrips (*Frankliniella intonsa*), rice thrips (*Stenchaetothrips biformis*), *Echinothrips americanus*, and the like;

from the family Phlaeothripidae, aculeated rice thrips (*Haplothrips aculeatus*), and the like.

Diptera:
- from the family Anthomyiidae, seedcorn maggot (*Delia platura*), onion maggot (*Delia antiqua*), beet leaf miner (*Pegomya cunicularia*), and the like;
- from the family Ulidiidae, sugarbeet root maggot (*Tetanops myopaeformis*), and the like;
- from the family Agromyzidae, rice leaf miner (*Agromyza oryzae*), tomato leaf miner (*Liriomyza sativae*), chrysanthemum leaf miner (*Liriomyza trifolii*), pea leafminer (*Chromatomyia horticola*), and the like;
- from the family Chloropidae, rice stem maggot (*Chlorops oryzae*), and the like;
- from the family Tephritidae, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*) Mediterranean fruit fly (*Ceratitis capitata*), apple maggot (*Rhagoletis pomonella*), Japanese cherry fruit fly (*Rhacochlaena japonica*), and the like;
- from the family Ephydridae, smaller rice leaf miner (*Hydrellia griseola*), whorl maggot (*Hydrellia philippina*), paddy stem maggot (*Hydrellia sasakii*), and the like;
- from the family Drosophilidae, cherry drosophila (*Drosophila suzukii*), and the like;
- from the family Phoridae, *Megaselia spiracularis*, and the like;
- from the family Psychodidae, *Clogmia albipunctata*, and the like;
- from the family Sciaridae, *Bradysia difformis*, and the like;
- from the family Cecidomyiidae, hessian fly (*Mayetiola destructor*), paddy gall fly (*Orseolia oryzae*), and the like;
- from the family Diopsidae, *Diopsis macrophthalma*, and the like;
- from the family Tipulidae, rice crane fly (*Tipula aino*), Common cranefly (*Tipula oleracea*), European cranefly (*Tipula paludosa*), and the like;
- from the family Culicidae, southern house mosquito (*Culex pipiens pallens*), *Culex tritaeniorhynchus*, *Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae*, *Anopheles stephensi*, *Anopheles coluzzii*, *Anopheles albimanus*, *Anopheles sundaicus*, *Anopheles arabiensis*, *Anopheles funestus*, *Anopheles darlingi*, *Anopheles farauti*, *Anopheles minimus*, and the like;
- from the family Simulidae, *Prosimulium yezoensis*, *Simulium ornatum*, and the like;
- from the family Tabanidae, *Tabanus trigonus*, and the like;
- from the family Muscidae, house fly (*Musca domestica*), false stable fly (*Muscina stabulans*), biting house fly (*Stomoxys calcitrans*), buffalo fly (*Haematobia irritans*), and the like;
- from the family Calliphoridae;
- from the family Sarcophagidae;
- from the family Chironomidae, *Chironomus plumosus*, *Chironomus yoshimatsui*, *Glyptotendipes tokunagai*, and the like;
- from the family Fannidae.

Coleoptera:
- from the family Chrysomelidae, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, tobacco flea beetle (*Epitrix hirtipennis*), and the like;
- from the family Carabidae, Seedcorn beetle (*Stenolophus lecontei*), Slender seedcorn beetle (*Clivina impressifrons*), and the like;
- from the family Scarabaeidae, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus*, *Holotrichia* spp., *Phyllophaga* spp. (such as June beetle (*Phyllophaga crinita*)), and *Diloboderus* spp. (such as *Diloboderus abderus*), and the like;
- from the family Curculionidae, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineatocollis*, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), cotton root borer (*Eutinobothrus brasiliensis*), and the like;
- from the family Tenebrionidae, red meal beetle (*Tribolium castaneum*), mason beetle (*Tribolium confusum*), lesser mealworm (*Alphitobius diaperinus*), and the like;
- from the family Coccinellidae, twenty-eight-spotted ladybird (*Epilachna vigintioctopunctata*), and the like;
- from the family Bostrychidae, common powder-post beetle (*Lyctus brunneus*), lesser grain borer (*Rhizopertha dominica*) and the like;
- from the family Ptinidae;
- from the family Cerambycidae, citrus long-horned beetle (*Anoplophora malasiaca*), *Migdolus fryanus*, and the like;
- from the family Elateridae, *Melanotus okinawensis*, barley wireworm (*Agriotes fuscicollis*), *Melanotus lega-*

*tus*, *Anchastus* spp., *Conoderus* spp., *Ctenicera* spp., *Limonius* spp., *Aeolus* spp., and the like;

from the family Staphylinidae, *Paederus fuscipes*, and the like;

from the family Dermestidae, varied carpet beetle (*Anthrenus verbasci*), hide beetle (*Dermestes maculates*), khapra beetle (*Trogoderma granarium*), and the like;

from the family Anobidae, tobacco beetle (*Lasioderma serricorne*) and biscuit beetle (*Stegobium paniceum*), and the like;

from the family Laemophloeidae, flat grain beetle (*Cryptolestes ferrugineus*), and the like;

from the family Silvanidae, saw-toothed grain beetle (*Oryzaephilus surinamensis*), and the like.

Orthoptera:

from the family Acrididae, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*), Japanese grasshopper (*Oxya yezoensis*) rice grasshopper (*Oxya japonica*), Bombay locust (*Patanga succincta*), and the like;

from the family Gryllotalpidae, oriental mole cricket (*Gryllotalpa orientalis*), and the like;

from the family Gryllidae, house cricket (*Acheta domestica*), emma field cricket (*Teleogryllus emma*), and the like;

from the family Tettigoniidae, for example, Mormon cricket (*Anabrus simplex*), and the like.

Hymenoptera:

from the family Tenthredinidae, beet sawfly (*Athalia rosae*), nippon cabbage sawfly (*Athalia japonica*), and the like;

from the family Formicidae, *Solenopsis* spp. (such as red imported fire ant (*Solenopsis invicta*), tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica fusca japonica*, *Pristomyrmex punctutus*, *Pheidole noda*, big-headed ant (*Pheidole megacephala*), *Camponotus* spp. (such as *Camponotus japonicus*, *Camponotus obscuripes*), *Pogonomyrmex* spp. (such as western harvester ant (*Pogonomyrmex occidentalis*)), *Wasmania* spp. (such as *Wasmania auropunctata*), long-legged ant (*Anoplolepis gracilipes*), and the like;

from the family Vespidae, Asian giant hornet (*Vespa mandarinia japonica*), *Vespa simillima*, *Vespa analis fabriciusi*, Asian hornet (*Vespa velutina*), *Polistes jokahamae*, and the like;

from the family Siricidae, pine wood wasp (*Urocerus gigas*), and the like;

from the family Bethylidae.

Blattodea:

from the family Blattellidae, German cockroach (*Blattella germanica*), and the like;

from the family Blattidae, smoky-brown cockroach (*Periplaneta fuliginosa*), American cockroach (*Periplaneta americana*), brown cockroach (*Periplaneta brunnea*), black cockroach (*Blatta orientalis*), and the like;

from the family Termitidae, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, *Cornitermes cumulans*, and the like.

Siphonaptera:

*Pulex* spp. (such as human flea (*Pulex irritans*)), *Ctenocephalides* spp. (such as cat flea (*Ctenocephalides felis*), dog flea (*Ctenocephalides canis*)), *Xenopsylla* spp. (such as oriental rat flea (*Xenopsylla cheopis*)), *Tunga* spp. (such as chigoe flea (*Tunga penetrans*)), *Echidnophaga* spp. (such as chicken flea (*Echidnophaga gallinacea*)), *Nosopsyllus* spp. (such as European rat flea (*Nosopsyllus fasciatus*)).

Psocodae:

*Pediculus* spp. (such as head louse (*Pediculus humanus capitis*)); *Phtirus* spp. (such as crab louse (*Pthirus pubis*)); *Haematopinus* spp. (such as short-nosed cattle louse (*Haematopinus eurysternus*), pig louse (*Haematopinus suis*)); *Damalinia* spp. (such as *Damalinia ovis*, *Damalinia bovis*); *Linognathus* spp. (such as blue cattle louse (*Linognathus vituli*), sheep face louse (*Linognathus ovillus*)); *Solenopotes* spp. (such as capillate louse (*Solenopotes capillatus*)); *Menopon* spp. (such as common chicken louse (*Menopon gallinae*)); *Trimenopon* spp.; *Trinoton* spp.; *Trichodectes* spp. (such as dog biting louse (*Trichodectes canis*)); *Felicola* spp. (such as cat louse (*Felicola subrostratus*)); *Bovicola* spp. (such as cattle biting louse (*Bovicola bovis*)); *Menacanthus* spp. (such as chicken body louse (*Menacanthus stramineus*)); *Werneckiella* spp.; *Lepikentron* spp.;

from the family Liposcelididae, book louse (*Liposcelis subfuscas*), *Liposcelis bostrychophilus*, *Liposcelis simulans*, *Liposcelis divinatorius*, *Liposcelis entomophila*, and the like.

Thysanura:

from the family Lepismatidae, oriental silverfish (*Ctenolepisma villosa*), moth fish (*Lepisma saccharina*), and the like.

Acari:

from the family Tetranychidae, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), *Oligonychus* spp., and the like;

from the family Eriophyidae, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, *Shevtchenkella* sp., and the like;

from the family Tarsonemidae, broad mite (*Polyphagotarsonemus latus*), and the like;

from the family Tenuipalpidae, *Brevipalpus phoenicis*, and the like;

from the family Tuckerellidae;

from the family Ixodidae, for example, *Haemaphysalis* spp. (such as *Haemaphysalis longicornis, Haemaphysalis flava, Haemaphysalis campanulata*), *Dermacentor* spp. (such as American dog tick (*Dermacentor variabilis*), *Dermacentor taiwanicus*, Rocky Mountain wood tick (*Dermacentor andersoni*)), *Ixodes* spp. (such as *Ixodes ovatus, Ixodes persulcatus*, black-legged tick (*Ixodes scapularis*), *Ixodes pacificus, Ixodes holocyclus*), *Amblyomma* spp. (such as lone star tick (*Amblyomma americanum*), gulf coast tick (*Amblyomma maculatum*)), *Boophilus* spp. (such as *Rhipicephalus (Boophilus) microplus, Boophilus annulatus*), and *Rhipicephalus* spp. (such as brown dog tick (*Rhipicephalus sanguineus*), *Rhipicephalus appendiculatus*);

from the family Acaridae, cereal mite (*Tyrophagus putrescentiae*), grassland mite (*Tyrophagus similis*), and the like;

from the family Pyroglyphidae, American house dust mite (*Dermatophagoides farinae*), European house dust mite (*Dermatophagoides pteronyssinus*), and the like;

from the family Cheyletidae, *Cheyletus eruditus, Cheyletus malaccensis, Chelacaropsis moorei, Cheyletiella yasguri*, and the like;

*Argas* spp. (such as fowl tick (*Argas persicus*)), *Ornithodorus* spp. (such as *Ornithodorus hermsi, Ornithodorus turicata*), *Psoroptes* spp. (such as sheep scab mite (*Psoroptes ovis*), horse psoroptic mange mite (*Psoroptes equi*)), *Knemidocoptes* spp. (such as *Knemidocoptes mutans*), *Notoedres* spp. (such as *Notoedres cati, Notoedres muris*), *Sarcoptes* spp. (such as itch mite (*Sarcoptes scabiei*)), *Otodectes* spp. (such as ear mange mite (*Otodectes cynotis*)), *Listrophorus* spp. (such as *Listrophorus gibbus*), *Chorioptes* spp., *Hypodectes* spp., *Pterolichus* spp., *Cytodites* spp., *Laminosioptes* spp., *Dermanyssus* spp. (such as bird mite (*Dermanyssus gallinae*)), *Ornithonyssus* spp. (such as feather mite (*Ornithonyssus sylviarum*), tropical rat mite (*Ornithonyssus bacoti*)), *Varroa* spp. (such as *Varroa jacobsoni*), *Cheyletiella* spp. (such as *Cheyletiella yasguri, Cheyletiella blakei*), *Ornithocheyletia* spp., *Demodex* spp. (such as dog follicle mite (*Demodex canis*), cat follicle mite (*Demodex cati*)), *Myobia* spp., *Psorergates* spp., *Trombicula* spp. (such as *Trombicula akamushi, Trombicula pallida, Trombicula scutellaris*).

Araneae:
from the family Eutichuridae, *Cheiracanthium japonicum*, and the like;
from the family Theridiidae, red-back spider (*Latrodectus hasseltii*), and the like.

Polydesmida:
from the family Paradoxosomatidae, flat-backed millipede (*Oxidus gracilis*), *Nedyopus tambanus*, and the like;

Isopoda:
from the family Armadillidiidae, common pill bug (*Armadillidium vulgare*), and the like;

Chilopoda:
from the family Scutigeridae, *Thereuonema hilgendorfi*, and the like;
from the family Scolopendridae, giant tropical centipede (*Scolopendra subspinipes*), and the like;
from the family Ethopolyidae, *Bothropolys rugosus*, and the like;

Gastropoda:
from the family Limacidae, tree slug (*Limax marginatus*), garden tawny slug (*Limax flavus*), and the like;
from the family Philomycidae, *Meghimatium bilineatum*, and the like;
from the family Ampullariidae, golden apple snail (*Pomacea canaliculata*), and the like;
from the family Lymnaeidae, *Austropeplea ollula*, and the like.

Nematoda:
from the family Aphelenchoididae, rice white-tip nematode (*Aphelenchoides besseyi*), and the like;
from the family Pratylenchidae, root lesion nematode (*Pratylenchus coffeae*), *Pratylenchus brachyurus*, California meadow nematode (*Pratylenchus neglectus*), *Radopholus similis*, and the like;
from the family Heteroderidae, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), white potato cyst nematode (*Globodera pallida*), and the like;
from the family Hoplolaimidae, *Rotylenchulus reniformis*, and the like;
from the family Anguinidae, strawberry bud nematode (*Nothotylenchus acris*), stem nematode (*Ditylenchus dipsaci*), and the like;
from the family Tylenchulidae, citrus nematode (*Tylenchulus semipenetrans*), and the like;
from the family Longidoridae, dagger nematode (*Xiphinema index*), and the like;
from the family Trichodoridae;
from the family Parasitaphelenchidae, pine wilt disease (*Bursaphelenchus xylophilus*), and the like.

The target harmful insects, harmful mites, harmful mollusks and harmful nematodes may have a reduced agent-sensitivity to or a developed agent-resistance to an insecticide, a miticide, a molluscicide or a nematicide. However, when the agent-sensitivity is greatly reduced or the agent-resistance is greatly developed, a composition of the present invention comprising an insecticide, a miticide, a molluscicide, and a nematicide other than the intended insecticide, miticide, molluscicide, and nematicide is preferably used.

The method for controlling harmful arthropods of the present invention is conducted by applying an effective amount of the present compound or the composition A to a harmful arthropod directly and/or a habitat where the harmful arthropod lives (for example, plant bodies, soil, an interior of a house, and animal bodies). Examples of a method for controlling harmful arthropods of the present invention include foliar application, soil application, root application, shower application, smoking application, water-surface application, and seed application.

The present compound or the composition A is usually mixed with an inert carrier such as solid carrier, liquid carrier or gaseous carrier, and if necessary, added with surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, and tablets and the others. Such formulations may be processed into mosquito repellent coils, electric mosquito repellent mats, liquid mosquito formulations, smoking agents, fumigants, sheet formulations, spot-on formulations or formulations for oral treatment. In these formulations, the present compound or the composition A is contained usually within a range of 0.0001 to 95% by weight.

Examples of the solid carrier to be used in the formulation include fine powders or granules of clays (for example, kaolin clay, diatomaceous earth, bentonite, Fubasami clay, or acid white clay), dry silica, wet silica, hydrated silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl etheR14-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseed oil).

Examples of gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of a base material of the resin formulation include polyvinyl chloride polymers, polyurethane, and the others, and a plasticizer such as phthalate esters (for example, dimethyl phthalate, and dioctyl phthalate), adipic acid esters and stearic acid may be added to the base material, if necessary. The resin formulation can be prepared by kneading the present compound in the base material with a conventional kneading machine, and then molding it by injection molding, extrusion molding, or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

As used herein, examples of the plant include whole plant, stem and leaf, flower, ear, fruit, tree stem, branch, crown, seed, vegetative reproductive organ, and seedling.

The vegetative reproductive organ represents a part of plant such as root, stem and leaf, which has a growth capacity if the part is cut off from its plant and then placed in the soil. Examples of the vegetative reproductive organ include tuberous root, creeping root, bulb, corm or solid bulb, tuber, rhizome, stolon, rhizophore, cane cuttings, propagule, and vine cutting. The "stolon" is often referred to as "runner", and the "propagule" is often referred to as "brood bud", which is divided into broad bud and bulbil. The vine cutting represents a shoot (which is a generic name of leaf and stem) of sweet potato (*Ipomoea batatas*) and Japanese yam (*Dioscorea japonica*), etc. The bulb, corm or solid bulb, tuber, rhizome, cane cuttings, rhizophore, and tuberous root are also collectively referred to as "bulb". For example, when the cultivation of potato starts with planting tubers in the soil, the used tuber is generally referred to as "seed potato".

Examples of a method for controlling harmful arthropods by applying an effective amount of the present compound or the composition A to soils include a method of applying an effective amount of the present compound or the composition A to soils before planting plants or after planting plants, a method of applying an effective amount of the present compound or the composition A to a root part of a crop to be protected from damage such as ingestion by harmful arthropods, and a method of controlling harmful arthropods that ingest a plant by permeating and transferring an effective amount of the present compound or the composition A from a root into the interior of the plant body. Specifically, examples of the application method include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering with soils), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

As used herein, seeds or vegetative reproductive organs carrying the present compound or the composition A means seeds or vegetative reproductive organs in the state where the present compound or the composition A is adhered to a surface of the seeds or the vegetative reproductive organ. Also, the present compound or the composition A which are may be adhered on the surface of the seeds or the vegetative reproductive organ may be permeated from the surface to the interior of the plant.

Also, when the composition A is adhered on the surface of the seeds or the vegetative reproductive organs, a layer consisting of single active ingredient may be multiply overlapped, a plural of the active ingredients may be mixed to form a single layer, a layer consisting of the single active ingredient and a layer consisting of the plural of the active ingredients may be multiply overlapped, or a layer consisting of the plural of the active ingredients may be multiply overlapped.

In the seeds or vegetative reproductive organs used for the seed treatment, any materials other than the present compound or the composition A may be adhered before or after being treated with the present compound or the composition A.

Examples of the application to seeds (or seed treatments) include an application of the present compound or the composition A to seeds or vegetative reproductive organs, and specific examples thereof include spraying treatment in which a suspension of the present compound or the composition A is sprayed onto seed surface or the vegetative reproductive organ surface in the form of mist; smearing treatment in which the present compound or the composition A is coated a surface of seeds or the vegetative reproductive organ; a soaking treatment in which the seeds are soaked into the solution of the present compound or the composition A for a certain time; and a method for coating the seeds or the vegetative reproductive organ with a carrier containing the present compound or the composition A (film coating treatment, pellet coating treatment). Examples of the above-described vegetative reproductive organ include particularly seed potato.

When the composition A is applied to seeds or vegetative reproductive organs, the composition A may be also applied to seeds or vegetative reproductive organs as a single formulation, or the composition A may be applied to seeds or vegetative reproductive organs as a divided plural of formulations by a plurality of times. Examples of the method in which the composition A is applied as a divided plural of formulations by a plurality of times include, for example, a method in which the formulations comprising as an active component the present compound only are applied, and seeds or vegetative reproductive organs are air dried, followed by applying the formulations comprising the present ingredient: and a method in which the formulations comprising as an active component the present compound and the present ingredients are applied, and seeds or vegetative reproductive organs are air dried, followed by applying the formulations comprising the present ingredients other than the already-applied present ingredients, are included.

When the present compound or the composition A is applied for harmful arthropods control in agricultural fields, the application dose thereof is usually within a range of 1 to 10,000 g of the present compound per 10,000 $m^2$. In the case of being applied to seeds or vegetative reproductive organs, the dose of application dose thereof is usually within a range of 0.001 to 100 g of the present compound per 1 Kg of seeds. When the present compound, the present compound X, or the composition A is formulated into an emulsifiable concentrate, a wettable powder or a flowable etc., they are usually applied by diluting them with water so as to make an effective concentration of the active ingredients 0.01 to 10,000 ppm, and the dust formulation or the granular formulation, etc., is usually applied as itself without diluting them.

Also, the resin formulation processed into a sheet shape or string shape may be wrapped around a crop, stretched near a crop, spread on a foot soil of a plant, or the like.

When the present compound or the composition A is used to control harmful arthropods that live inside a house, an applied dose as an amount of the present compound is usually within a range from 0.01 to 1,000 mg per 1 $m^2$ of an area to be treated, in the case of using it on a planar area. In the case of using it spatially, the applied dose as an amount of the present compound is usually within a range from 0.01 to 500 mg per 1 $m^3$ of the space to be treated. When the present compound or the composition A is formulated into emulsifiable concentrates, wettable powders, flowables or the others, the formulation is usually applied after diluting it with water in such a way that a concentration of the active ingredient is within a range from 0.1 to 10,000 ppm, and then sparging it. In the case of being formulated into oil solutions, aerosols, smoking agents, poison baits and the others, the formulation is used as itself without diluting it.

When the present compound or the composition A is used for controlling external parasites of livestock such as cows, horses, pigs, sheep, goats and chickens, and small animals such as dogs, cats, rats and mice, the present composition can be applied to the animal by a known method in the veterinary field. Specifically, when systemic control is intended, the present composition is administered to the animal as a tablet, a mixture with feed or a suppository, or by injection (including intramuscular, subcutaneous, intravenous and intraperitoneal injections). On the other hand, when non-systemic control is intended, the present composition is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound is usually within a range from 0.1 to 1,000 mg per 1 kg of a body weight of the animal.

Further, the present compound, or the composition A can be used as an agent for controlling harmful arthropods in the agricultural land such as field, paddy, lawn and orchard. Examples of the plants include the following plants.

Corn, rice, wheat, barley, rye, oat, sorghum, cotton, soybean, peanut, buckwheat, beet, rapeseed, sunflower, sugarcane, tobacco, solanaceous vegetables (for example, eggplant, tomato, green pepper, hot pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, pomaceous fruits (for example, apple, pear, Japanese pear, Chinese quince, and quince), stone fleshy fruits (for example, peach, plum, nectarine, *Prunus mume*, cherry fruit, apricot, and prune), citrus fruits (for example, *Citrus unshiu*, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, tea, mulberry, foliage plants, forest plants, pteridophytes, grasses.

The above plants also include a plant that can be generated by a natural crossbreeding, a plant that can be generated by mutations, an F1 hybrid plant, and a genetically modified crop. Examples of the genetically modified crop include a plant modified to have the resistance to HPPD (4-hydroxyphenylpyruvate dioxygenase) inhibitors such as isoxaflutole, ALS (acetolactate synthase) inhibitors such as imazethapyr and thifensulfuron-methyl, EPSP (5-enolpyruvoylshikimate-3-phosphate synthase) inhibitors, glutamine synthetase inhibitors, PPO (protoporphyrinogen oxidase) inhibitors, or herbicides such as bromoxynil and dicamba; a plant modified to synthesize a selective toxin known to be produced in *Bacillus* such as *Bacillus thuringiensis*; and a plant modified to have a specific insecticidal activity by synthesizing a gene fragment partially corresponding to an endogenous gene derived from a harmful insect to induce the gene silencing (RNAi; RNA interference) in the target harmful insect.

The above-mentioned plants are not limited specifically, as long as they are breeds that are usually cultivated.

EXAMPLES

Hereinafter, the present invention is explained in more detail by using Preparation examples, Reference preparation examples, and Test examples, however, the present invention should not be limited to these examples.

As used herein, "Me" represents a methyl group, "Et" represents an ethyl group, "Pr" represents a propyl group, "i-Pr" represents an isopropyl group, "c-Pr" represents a cyclopropyl group, "c-Bu" represents a cyclobutyl group, "c-Pen" represents a cyclopentyl group, "c-Hex" represents a cyclohexyl group, "Ph" represents a phenyl group, "Py2" represents a 2-pyridyl group, "Py3" represents a 3-pyridyl group, "Py4" represents a 4-pyridyl group, "Bn" represents benzyl group. When c-Pr, c-Bu, c-Pen, c-Hex, Ph, Py2, Py3, and Py4 have a substituent, the substituent is written with its substituted position before the symbol. For example, "1-CN-c-Pr" represents a 1-cyanocyclopropyl group, "3,4-F$_2$-Ph" represents a 3,4-difluorophenyl group, "4-CF$_3$-Py2" represents a 4-(trifluoromethyl)-2-pyridyl group, and "5-OCH$_2$CF$_2$CF$_3$-Py2" represents a 5-(2,2,3,3,3-pentafluoropropoxy)-2-pyridyl group.

Firstly, a preparation example of the present compound is shown.

Preparation Example 1

A mixture of 4-(2,2,3,3,3-pentafluoropropoxy)pyridine-2-ol 0.24 g, 5-bromo-3-(ethanesulfonyl)-2-fluoropyridine 0.27 g, cesium carbonate 0.39 g and toluene 3 mL was stirred at 100° C. for 4.5 hours. The resulting mixture was stood to cool to room temperature, and thereto was added saturated brine, and the mixture was extracted with ethyl acetate. The resulting organic layer was dried over anhydrous sodium sulfate and concentrated under reduced pressure. The resulting residue was subjected to a silica gel column chromatography (hexane:ethyl acetate=1:1) to obtain the present compound 1 represented by the following formula 0.23 g.

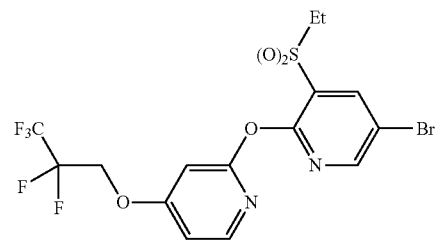

Present compound 1: $^1$H-NMR (CDCl$_3$) δ: 8.50 (1H, d), 8.47 (1H, d), 8.21 (1H, d), 6.84 (1H, dd), 6.72 (1H, d), 4.50 (2H, t), 3.48 (2H, q), 1.36 (3H, t).

Preparation Example 1A

The compounds which were prepared according to the method described in the preparation example 1 and their physical property values are shown below.

A compound represented by formula (A-1):

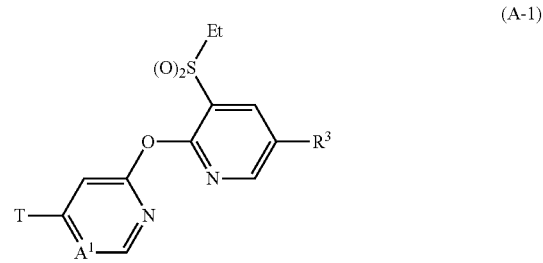

(A-1)

wherein a combination of T, A$^1$, R$^3$ and n represents any combinations described in [Table A1].

TABLE A1

| Present compound | T | A1 | R$^3$ | n |
|---|---|---|---|---|
| 2 | OCH$_2$CF$_2$CF$_3$ | CH | CF$_3$ | 2 |
| 3 | OCH$_2$CF$_2$CF$_3$ | CH | H | 2 |
| 4 | OCH$_2$CF$_2$CF$_3$ | CH | H | 0 |
| 5 | OCH$_2$CF$_2$CF$_3$ | CH | H | 1 |
| 6 | OCH$_2$CF$_2$CF$_3$ | N | S(O)$_2$Et | 2 |

TABLE A1-continued

| Present compound | T | A1 | R³ | n |
|---|---|---|---|---|
| 7 | OCH₂CF₂CF₃ | N | CF₃ | 2 |
| 8 | CF₃ | CH | H | 2 |
| 9 | CF₃ | CH | CF₃ | 2 |
| 10 | F₃C-pyrazolyl | CH | H | 2 |
| 11 | OCH₂CF₂CF₃ | N | Cl | 2 |
| 12 | OCH₂CF₂CF₃ | N | Br | 2 |
| 15 | OCH₂CF₂CF₃ | N | c-Pr | 2 |
| 16 | OCH₂CF₂CF₃ | N | H | 2 |
| 17 | OCH₂CF₂CF₃ | CH | 1-CN-c-Pr | 2 |
| 18 | OCH₂CF₂CF₃ | N | 1-CN-c-Pr | 2 |
| 19 | OCH₂CF₂CF₃ | CH | 1-CN-c-Pen | 2 |
| 20 | OCH₂CF₂CF₃ | CH | 1-CN-c-Hex | 2 |
| 21 | OCH₂CF₂CF₃ | N | 1-CN-c-Bu | 2 |
| 22 | OCH₂CF₂CF₃ | N | 1-CN-c-Pen | 2 |
| 23 | OCH₂CF₂CF₃ | N | 1-CN-c-Hex | 2 |
| 24 | OCH₂C(Me)₂CN | N | c-Pr | 2 |
| 26 | OCH₂(1-CN-c-Pr) | N | H | 2 |
| 28 | OCH₂CF₂CHF₂ | N | 1-CN-c-Pr | 2 |

Present compound 2: $^1$H-NMR (CDCl$_3$) δ: 8.65-8.64 (2H, m), 8.26 (1H, d), 6.90 (1H, dd), 6.77 (1H, d), 4.52 (2H, dd), 3.53 (2H, q), 1.38 (3H, dd).

Present compound 3: $^1$H-NMR (CDCl$_3$) δ: 8.44 (1H, dd), 8.41 (1H, dd), 8.24 (1H, d), 7.31 (1H, dd), 6.84 (1H, dd), 6.73 (1H, d), 4.50 (2H, t), 3.50 (2H, q), 1.35 (3H, t).

Present compound 4: $^1$H-NMR (CDCl$_3$) δ: 8.15-8.09 (2H, m), 7.68 (1H, dd), 7.12 (1H, dd), 6.71 (1H, dd), 6.63 (1H, d), 4.48 (2H, td), 2.97 (2H, q), 1.34 (3H, t).

Present compound 5: $^1$H-NMR (CDCl$_3$) δ: 8.32 (1H, dd), 8.28 (1H, dd), 8.22 (1H, d), 7.36 (1H, dd), 6.80 (1H, dd), 6.67 (1H, d), 4.53-4.47 (2H, m), 3.22 (1H, dt), 2.96 (1H, dt), 1.28 (3H, t).

Present compound 6: $^1$H-NMR (CDCl$_3$) δ: 8.92 (1H, d), 8.85 (1H, d), 8.60 (1H, s), 6.76 (1H, s), 4.97 (2H, t), 3.49 (2H, q), 3.24 (2H, q), 1.38-1.36 (6H, m).

Present compound 7: $^1$H-NMR (CDCl$_3$) δ: 8.75-8.74 (1H, m), 8.67-8.67 (1H, m), 8.58 (1H, d), 6.73 (1H, d), 4.97-4.94 (2H, m), 3.48 (2H, q), 1.37 (3H, t).

Present compound 8: $^1$H-NMR (CDCl$_3$) δ: 8.52 (1H, d), 8.45-8.44 (2H, m), 7.44 (1H, d), 7.43 (1H, s), 7.35 (1H, dd), 3.50 (2H, q), 1.36 (3H, t).

Present compound 9: $^1$H-NMR (CDCl$_3$) δ: 8.66 (2H, s), 8.55 (1H, d), 7.52 (1H, d), 7.46 (1H, s), 3.54 (2H, q), 1.40 (3H, t).

Present compound 10: $^1$H-NMR (CDCl$_3$) δ: 8.45-8.43 (3H, m), 8.11-8.10 (1H, m), 7.63 (1H, dd), 7.57 (1H, d), 7.34 (1H, dd), 6.80 (1H, d), 3.52 (2H, q), 1.36 (3H, t).

Present compound 11: $^1$H-NMR (CDCl$_3$) δ: 8.54 (1H, d), 8.47 (1H, d), 8.41 (1H, d), 6.64 (1H, d), 4.95-4.91 (2H, m), 3.42 (2H, q), 1.35 (3H, t).

Present compound 12: $^1$H-NMR (CDCl$_3$) δ: 8.57 (1H, d), 8.53 (1H, d), 8.53 (1H, d), 6.64 (1H, d), 4.95-4.91 (2H, m), 3.42 (2H, q), 1.35 (3H, t).

Present compound 15: $^1$H-NMR (CDCl$_3$) δ: 8.51 (1H, d), 8.34 (1H, d), 8.01 (1H, d), 6.58 (1H, d), 4.93-4.89 (2H, m), 3.40 (2H, q), 2.05-1.98 (1H, m), 1.32 (3H, t), 1.17-1.12 (2H, m), 0.83-0.81 (2H, m).

Present compound 16: $^1$H-NMR (CDCl$_3$) δ: 8.80 (1H, d), 8.53 (1H, dd), 8.32 (1H, dd), 7.90 (1H, dd), 6.56 (1H, d), 4.97-4.93 (2H, m), 3.52 (2H, q), 1.32 (3H, t).

Present compound 17: $^1$H-NMR (CDCl$_3$) δ: 8.52 (1H, d), 8.22 (1H, d), 8.18 (1H, d), 6.84 (1H, dd), 6.73 (1H, d), 4.50 (2H, t), 3.49 (2H, q), 1.86-1.85 (2H, m), 1.49-1.47 (2H, m), 1.36 (3H, t).

Present compound 18: $^1$H-NMR (CDCl$_3$) δ: 8.61 (1H, d), 8.53 (1H, s), 8.19 (1H, d), 6.65 (1H, s), 4.93 (2H, t), 3.43 (2H, q), 1.91-1.89 (2H, m), 1.54-1.52 (2H, m), 1.35 (3H, t).

Present compound 19: $^1$H-NMR (CDCl$_3$) δ: 8.57 (1H, d), 8.38 (1H, d), 8.24 (1H, d), 6.85 (1H, dd), 6.74 (1H, d), 4.50 (2H, t), 3.51 (2H, q), 2.57-2.56 (2H, m), 2.10-1.99 (6H, m), 1.37 (3H, t).

Present compound 20: $^1$H-NMR (CDCl$_3$) δ: 8.62 (1H, d), 8.40 (1H, d), 8.24 (1H, d), 6.85 (1H, dd), 6.74 (1H, d), 4.50 (2H, t), 3.51 (2H, q), 2.20 (2H, d), 2.01-1.77 (8H, m), 1.37 (3H, t).

Present compound 21: $^1$H-NMR (CDCl$_3$) δ: 8.59 (1H, d), 8.55 (1H, d), 8.44 (1H, d), 6.67 (1H, d), 4.94 (2H, t), 3.45 (2H, q), 2.95-2.91 (2H, m), 2.71-2.66 (2H, m), 2.56-2.52 (1H, m), 2.20-2.16 (1H, m), 1.37 (3H, t).

Present compound 22: $^1$H-NMR (CDCl$_3$) δ: 8.67 (1H, d), 8.55 (1H, s), 8.41 (1H, d), 6.67 (1H, s), 4.93 (2H, t), 3.45 (2H, q), 2.60-2.58 (2H, m), 2.11-2.01 (6H, m), 1.36 (3H, t).

Present compound 23: $^1$H-NMR (C$_6$D$_6$) δ: 8.71 (1H, d), 8.55 (1H, d), 8.44 (1H, d), 6.67 (1H, d), 4.94 (2H, t), 3.45 (2H, q), 2.23 (2H, d), 1.95-1.83 (8H, m), 1.35 (3H, t).

Present compound 24: $^1$H-NMR (CDCl$_3$) δ: 8.48 (1H, s), 8.33 (1H, d), 8.01 (1H, d), 6.54 (1H, s), 4.35 (2H, s), 3.40 (2H, q), 2.01-1.99 (1H, m), 1.47 (6H, s), 1.32-1.30 (2H, m), 1.25 (3H, t), 1.15-1.13 (2H, m).

Present compound 26: $^1$H-NMR (CDCl$_3$) δ: 8.54 (1H, dd), 8.50 (1H, s), 8.45 (1H, dd), 7.41 (1H, dd), 6.61 (1H, s), 4.42 (2H, s), 3.45 (2H, q), 1.43-1.41 (2H, m), 1.33 (3H, t), 1.17-1.15 (2H, m).

Present compound 28: $^1$H-NMR (CDCl$_3$) δ: 8.60 (1H, d), 8.54 (1H, d), 8.19 (1H, d), 6.63 (1H, d), 5.98 (1H, tt), 4.85 (2H, t), 3.43 (2H, q), 1.91-1.89 (2H, m), 1.54-1.52 (2H, m), 1.35 (3H, t).

Preparation Example 3-1

An intermediate compound 1 represented by the following formula was prepared by using 4-iodopyridine-2-ol instead of 4-(2,2,3,3,3-pentafluoropropoxy)pyridine-2-ol according to the preparation example 1.

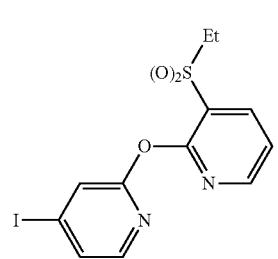

Intermediate compound 1: $^1$H-NMR (CDCl$_3$) δ: 8.38-8.42 (2H, m), 8.01 (1H, d), 7.56-7.58 (2H, m), 7.28-7.31 (1H, m), 3.46 (2H, q), 1.32 (3H, t).

Preparation Example 3-2

Under nitrogen atmosphere, a mixture of the intermediate compound 1 0.30 g, 3-(trifluoromethyl)phenyl boronic acid 0.16 g, 1,1'-bis(diphenylphosphino)ferrocene (II) palladium (II) dichloride 0.05 g, potassium carbonate 0.32 g, and 1,2-dimethoxyethane 5 mL and water 1 mL was stirred under reflux for 4 hours. The resulting mixture was stood to cool to room temperature, and thereto was added saturated brine, and the mixture were extracted with ethyl acetate. The resulting organic layers were derived over anhydrous sodium sulfate, and concentrated under reduced pressure. The resulting residue was subjected to a silica gel column chromatography (hexane:ethyl acetate=1:1) to obtain the present compound 11 represented by the following formula 0.17 g.

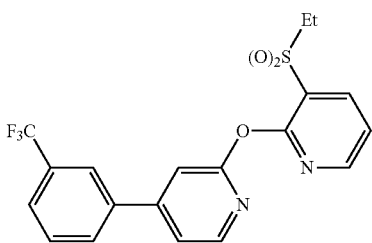

Present compound 11: $^1$H-NMR (CDCl$_3$) δ: 8.45-8.42 (3H, m), 7.90 (1H, s), 7.84 (1H, d), 7.73 (1H, d), 7.64 (1H, t), 7.46 (1H, dd), 7.41 (1H, d), 7.31 (1H, dd), 3.55 (2H, q), 1.37 (3H, t).

Preparation Example 4

To a mixture of the present compound 5 0.19 g, potassium tert-butoxide 67 mg, cyanamide 25 mg, and methanol 5 mL was added N-bromosuccinimide 0.14 g under ice-cooling, and the mixture was stirred under ice-cooling for 2 hours. Water was added to the resulting mixture, and the mixture was extracted with chloroform. The resulting organic layers was dried over anhydrous sodium sulfate, and concentrated under reduced pressure to obtain the present compound 13 represented by the following formula 0.27 g.

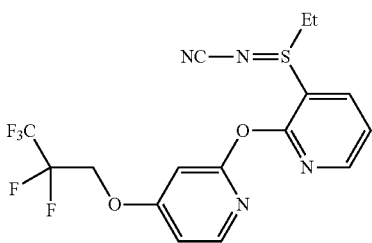 [SMILES: CCS(=NC#N)c1cccnc1Oc1cc(OCC(F)(F)C(F)(F)F)ccn1]

Present compound 13: $^1$H-NMR (CDCl$_3$) δ: 8.46 (1H, dd), 8.41 (1H, dd), 8.22 (1H, d), 7.41 (1H, dd), 6.85 (1H, dd), 6.73 (1H, d), 4.52 (2H, t), 3.48-3.45 (1H, m), 3.28-3.25 (1H, m), 1.46 (3H, t).

Preparation Example 5

To a mixture of the present compound 13 0.27 g, chloroform 2 mL and acetonitrile 2 mL was added ruthenium(III) chloride 10 mg under ice-cooling, and next thereto was added a solution of sodium periodate 0.2 g and water 3 mL. The resulting mixture was stirred vigorously at room temperature for 24 hours, and thereafter, thereto was added 2-propanol 2 mL, and the mixture was filtered through Celite (registered trademark). The resulting filtrates were extracted with ethyl acetate. The resulting organic layer was dried over anhydrous sodium sulfate, and concentrated under reduced pressure. The resulting residue was subjected to a silica gel column chromatography (hexane:ethyl acetate=1:1) to obtain the present compound 14 represented by the following formula 0.11 g.

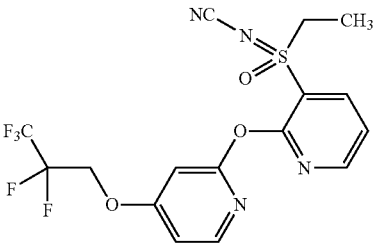 [SMILES: CCS(=O)(=NC#N)c1cccnc1Oc1cc(OCC(F)(F)C(F)(F)F)ccn1]

Present compound 14: $^1$H-NMR (CDCl$_3$) δ: 8.51 (1H, dd), 8.46 (1H, dd), 8.26 (1H, d), 7.40 (1H, dd), 6.90 (1H, dd), 6.86 (1H, d), 4.51 (2H, t), 3.85-3.75 (2H, m), 1.45 (3H, t).

Preparation Example 6

The present compound 25 was obtained by using the present compound 1 instead of the intermediate compound 1 and 4-cyanophenyl boronic acid instead of 3-(trifluoromethyl)phenyl boronic acid according to the preparation example 3-2.

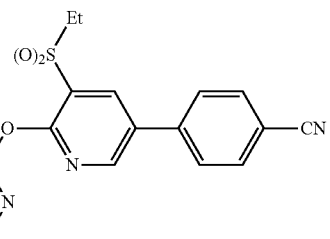

Present compound 25: $^1$H-NMR (CDCl$_3$) δ: 8.64 (1H, d), 8.59 (1H, d), 8.25 (1H, d), 7.81 (2H, d), 7.70 (2H, d), 6.86 (1H, dd), 6.78 (1H, d), 4.52 (2H, t), 3.54 (2H, q), 1.39 (3H, t).

Preparation Example 7

A mixture of the intermediate compound 1 0.30 g, 1-iodo-1,1,2,2,3,3,4,4,4-nonafluorobutane 3.0 g, copper powder 0.50 g, and NMP 5 mL was stirred at 120° C. for 6 hours. The resulting mixture was stood to cool to room temperature, and thereto was added saturated brine, and the mixture was extracted with ethyl acetate. The resulting organic layer was dried over anhydrous sodium sulfate, and concentrated under reduced pressure. The resulting residue was subjected to silica gel column chromatography (hexane:ethyl acetate=1:1) to obtain the present compound 27 represented by the following formula 0.04 g.

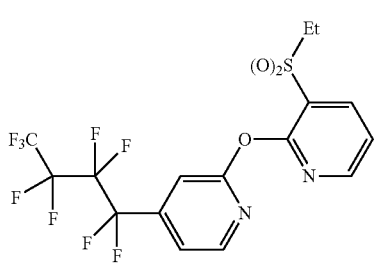

Present compound 27: ¹H-NMR (CDCl$_3$) δ: 8.53 (1H, d), 8.45-8.42 (2H, m), 7.42-7.40 (2H, m), 7.36-7.33 (1H, m), 3.50 (2H, q), 1.36 (3H, t).

Examples of the present compounds which are prepared according to any of the preparation examples described in Examples and the processes described herein are shown below.

A compound represented by formula (L-1):

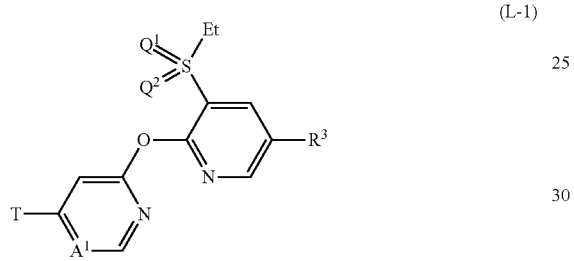

(hereinafter, referred to as "Compound (L-1)") wherein A$^1$ represents CH, Q$^1$ and Q$^2$ are absent, R$^3$ represents a hydrogen atom, and T represents any substituents described in [Table L1] to [Table L3]
(hereinafter, referred to as "Compound Class SX$_1$").

Table 2

TABLE L1

CF$_3$
CHF$_2$
CH$_2$CF$_3$
CF$_2$CF$_3$
CH$_2$CF$_2$CF$_3$
CF$_2$CF$_2$CF$_3$
CF$_2$CF$_2$CF$_2$CF$_3$
CF$_2$CF$_2$CF$_2$CF$_2$CF$_3$
OCF$_3$
OCHF$_2$
OCH$_2$CF$_3$
OCH$_2$CHF$_2$
OCF$_2$CF$_3$
OCH(CH$_3$)CF$_3$
OCH$_2$CF$_2$CHF$_2$
OCH$_2$CF$_2$CF$_3$
OCF$_2$CF$_2$CF$_3$
OCH$_2$CF$_2$CHFCF$_3$
OCH$_2$CF$_2$CF$_2$CF$_3$
OCF$_2$CF$_2$CF$_2$CF$_3$
OCH$_2$CF$_2$CF$_2$CF$_2$CF$_3$
OCH$_2$C(Me)$_2$CN
OCH$_2$(1-CN-c-Pr)
OCH$_2$(2,2-F$_2$-c-Pr)
OCH$_2$(1-CF$_3$-c-Pr)
OS(O)$_2$CF$_3$
OS(O)$_2$CF$_2$CF$_3$

TABLE L1-continued

OS(O)$_2$CF$_2$CF$_2$CF$_3$

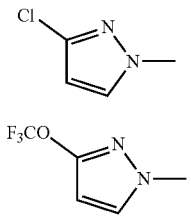

TABLE L2

SCF$_3$
SCH$_2$CF$_3$
SCF$_2$CF$_3$
SCH$_2$CF$_2$CF$_3$
SCF$_2$CF$_2$CF$_3$
SCH$_2$CF$_2$CF$_2$CF$_3$
SCF$_2$CF$_2$CF$_2$CF$_3$
S(O)CF$_3$
S(O)CH$_2$CF$_3$
S(O)CF$_2$CF$_3$
S(O)CH$_2$CF$_2$CF$_3$
S(O)CF$_2$CF$_2$CF$_3$
S(O)CH$_2$CF$_2$CF$_2$CF$_3$
S(O)CF$_2$CF$_2$CF$_2$CF$_3$
S(O)$_2$CF$_3$
S(O)$_2$CH$_2$CF$_3$
S(O)$_2$CF$_2$CF$_3$
S(O)$_2$CH$_2$CF$_2$CF$_3$
S(O)$_2$CF$_2$CF$_2$CF$_3$
S(O)$_2$CH$_2$CF$_2$CF$_2$CF$_3$
S(O)$_2$CF$_2$CF$_2$CF$_2$CF$_3$
NHCH$_2$CF$_3$
NHCH$_2$CF$_2$CF$_3$
NHCH$_2$CF$_2$CF$_2$CF$_3$
NMeCH$_2$CF$_3$
NMeCH$_2$CF$_2$CF$_3$
NMeCH$_2$CF$_2$CF$_2$CF$_3$
NEtCH$_2$CF$_3$

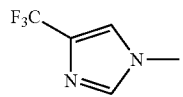

TABLE L3

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph
4-CF$_3$—Py2
5-CF$_3$—Py2
4-SCF$_3$—Py2
4-S(O)CF$_3$—Py2
4-S(O)$_2$CF$_3$—Py2
5-SCF$_3$—Py2
5-S(O)CF$_3$—Py2
5-S(O)$_2$CF$_3$—Py2
5-NMeCH$_2$CF$_3$—Py2
5-CF$_3$—Py3

TABLE L3-continued

6-CF$_3$—Py3
5-SCF$_3$—Py3
5-S(O)CF$_3$—Py3
5-S(O)$_2$CF$_3$—Py3
6-SCF$_3$—Py3
6-S(O)CF$_3$—Py3
6-S(O)$_2$CF$_3$—Py3
6-NMeCH$_2$CF$_3$—Py3
NEtCH$_2$CF$_2$CF$_3$

[Structure: F$_3$C-substituted pyrazole, N-linked]

[Structure: F$_3$C-substituted pyrazole isomer, N-linked]

A compound (L-1) wherein $A^1$ represents CH, $Q^1$ and $Q^2$ are absent, $R^3$ represents a trifluoromethyl group, and T represents any substituents described in [Table L1] to [Table L3] (hereinafter, referred to as "Compound Class SX$_2$").

A compound (L-1) wherein $A^1$ represents CH, $Q^1$ and $Q^2$ are absent, $R^3$ represents a cyclopropyl group, and T represents any substituents described in [Table L1] to [Table L3] (hereinafter, referred to as "Compound Class SX$_3$").

A compound (L-1) wherein $A^1$ represents CH, $Q^1$ and $Q^2$ are absent, $R^3$ represents a 1-cyanocyclopropyl group, and T represents any substituents described in [Table L1] to [Table L3] (hereinafter, referred to as "Compound Class SX$_4$").

A compound (L-1) wherein $A^1$ represents CH, $Q^1$ and $Q^2$ are absent, $R^3$ represents a chlorine atom, and T represents any substituents described in [Table L1] to [Table L3] (hereinafter, referred to as "Compound Class SX$_5$").

A compound (L-1) wherein $A^1$ represents CH, $Q^1$ represents an oxygen atom, $Q^2$ is absent, $R^3$ represents a hydrogen atom, and T represents any substituents described in [Table L1] to [Table L3] (hereinafter, referred to as "Compound Class SX$_6$")

A compound (L-1) wherein $A^1$ represents CH, $Q^1$ represents an oxygen atom, $Q^2$ is absent, $R^3$ represents a trifluoromethyl group, and T represents any substituents described in [Table L1] to [Table L3] (hereinafter, referred to as "Compound Class SX$_7$").

A compound (L-1) wherein $A^1$ represents CH, $Q^1$ represents an oxygen atom, $Q^2$ is absent, $R^3$ represents a cyclopropyl group, and T represents any substituents described in [Table L1] to [Table L3] (hereinafter, referred to as "Compound Class SX$_8$").

A compound (L-1) wherein $A^1$ represents CH, $Q^1$ represents an oxygen atom, $Q^2$ is absent, $R^3$ represents a 1-cyanocyclopropyl group, and T represents any substituents described in [Table L1] to [Table L3] (hereinafter, referred to as "Compound Class SX$_9$").

A compound (L-1) wherein $A^1$ represents CH, $Q^1$ represents an oxygen atom, $Q^2$ is absent, $R^3$ represents a chlorine atom, and T represents any substituents described in [Table L1] to [Table L3] (hereinafter, referred to as "Compound Class SX$_{10}$").

A compound (L-1) wherein $A^1$ represents CH, $Q^1$ represents N—CN, $Q^2$ is absent, $R^3$ represents a hydrogen atom, and T represents any substituents described in [Table L1] to [Table L3] (hereinafter, referred to as "Compound Class SX$_{11}$").

A compound (L-1) wherein $A^1$ represents CH, $Q^1$ represents N—CN, $Q^2$ is absent, $R^3$ represents a trifluoromethyl group, and T represents any substituents described in [Table L1] to [Table L3] (hereinafter, referred to as "Compound Class SX$_{12}$").

A compound (L-1) wherein $A^1$ represents CH, $Q^1$ represents N—CN, $Q^2$ is absent, $R^3$ represents a cyclopropyl group, and T represents any substituents described in [Table L1] to [Table L3] (hereinafter, referred to as "Compound Class SX$_{13}$").

A compound (L-1) wherein $A^1$ represents CH, $Q^1$ represents N—CN, $Q^2$ is absent, $R^3$ represents a 1-cyanocyclopropyl group, and T represents any substituents described in [Table L1] to [Table L3] (hereinafter, referred to as "Compound Class SX$_{14}$").

A compound (L-1) wherein $A^1$ represents CH, $Q^1$ represents N—CN, $Q^2$ is absent, $R^3$ represents a chlorine atom, and T represents any substituents described in [Table L1] to [Table L3] (hereinafter, referred to as "Compound Class SX$_{15}$").

A compound (L-1) wherein $A^1$ represents CH, $Q^1$ represents an oxygen atom, $Q^2$ is N—CN, $R^3$ represents a hydrogen atom, and T represents any substituents described in [Table L1] to [Table L3] (hereinafter, referred to as "Compound Class SX$_{16}$").

A compound (L-1) wherein $A^1$ represents CH, $Q^1$ represents an oxygen atom, $Q^2$ is N—CN, $R^3$ represents a trifluoromethyl group, and T represents any substituents described in [Table L1] to [Table L3] (hereinafter, referred to as "Compound Class SX$_{17}$").

A compound (L-1) wherein $A^1$ represents CH, $Q^1$ represents an oxygen atom, $Q^2$ is N—CN, $R^3$ represents a cyclopropyl group, and T represents any substituents described in [Table L1] to [Table L3] (hereinafter, referred to as "Compound Class SX$_{18}$").

A compound (L-1) wherein $A^1$ represents CH, $Q^1$ represents an oxygen atom, $Q^2$ is N—CN, $R^3$ represents a 1-cyanocyclopropyl group, and T represents any substituents described in [Table L1] to [Table L3] (hereinafter, referred to as "Compound Class SX$_{19}$").

A compound (L-1) wherein $A^1$ represents CH, $Q^1$ represents an oxygen atom, $Q^2$ is N—CN, $R^3$ represents a chlorine atom, and T represents any substituents described in [Table L1] to [Table L3] (hereinafter, referred to as "Compound Class SX$_{20}$").

A compound (L-1) wherein $A^1$ represents CH, $Q^1$ and $Q^2$ represent an oxygen atom, $R^3$ represents a hydrogen atom, and T represents any substituents described in [Table L1] to [Table L3] (hereinafter, referred to as "Compound Class SX$_{21}$").

A compound (L-1) wherein $A^1$ represents CH, $Q^1$ and $Q^2$ represent an oxygen atom, $R^3$ represents a trifluoromethyl group, and T represents any substituents described in [Table L1] to [Table L3] (hereinafter, referred to as "Compound Class SX$_{22}$").

A compound (L-1) wherein $A^1$ represents CH, $Q^1$ and $Q^2$ represent an oxygen atom, $R^3$ represents a cyclopropyl group, and T represents any substituents described in [Table L1] to [Table L3] (hereinafter, referred to as "Compound Class SX$_{23}$").

A compound (L-1) wherein $A^1$ represents CH, $Q^1$ and $Q^2$ represent an oxygen atom, $R^3$ represents a 1-cyanocyclopropyl group, and T represents any substituents described in [Table L1] to [Table L3] (hereinafter, referred to as "Compound Class SX$_{24}$").

A compound (L-1) wherein $A^1$ represents CH, $Q^1$ and $Q^2$ represent an oxygen atom, $R^3$ represents a chlorine atom, and T represents any substituents described in [Table L1] to [Table L3] (hereinafter, referred to as "Compound Class $SX_{25}$").

A compound (L-1) wherein $A^1$ represents a nitrogen atom, $Q^1$ and $Q^2$ are absent, $R^3$ represents a hydrogen atom, and T represents any substituents described in [Table L1] to [Table L3] (hereinafter, referred to as "Compound Class $SX_{26}$").

A compound (L-1) wherein $A^1$ represents a nitrogen atom, $Q^1$ and $Q^2$ are absent, $R^3$ represents a trifluoromethyl group, and T represents any substituents described in [Table L1] to [Table L3] (hereinafter, referred to as "Compound Class $SX_{27}$").

A compound (L-1) wherein $A^1$ represents a nitrogen atom, $Q^1$ and $Q^2$ are absent, $R^3$ represents a cyclopropyl group, and T represents any substituents described in [Table L1] to [Table L3] (hereinafter, referred to as "Compound Class $SX_{28}$").

A compound (L-1) wherein $A^1$ represents a nitrogen atom, $Q^1$ and $Q^2$ are absent, $R^3$ represents a 1-cyanocyclopropyl group, and T represents any substituents described in [Table L1] to [Table L3] (hereinafter, referred to as "Compound Class $SX_{29}$").

A compound (L-1) wherein $A^1$ represents a nitrogen atom, $Q^1$ and $Q^2$ are absent, $R^3$ represents a chorine atom, and T represents any substituents described in [Table L1] to [Table L3] (hereinafter, referred to as "Compound Class $SX_{30}$").

A compound (L-1) wherein $A^1$ represents a nitrogen atom, $Q^1$ represents an oxygen atom, $Q^2$ are absent, $R^3$ represents a hydrogen atom, and T represents any substituents described in [Table L1] to [Table L3] (hereinafter, referred to as "Compound Class $SX_{31}$").

A compound (L-1) wherein $A^1$ represents a nitrogen atom, $Q^1$ represents an oxygen atom, $Q^2$ are absent, $R^3$ represents a trifluoromethyl group, and T represents any substituents described in [Table L1] to [Table L3] (hereinafter, referred to as "Compound Class $SX_{32}$").

A compound (L-1) wherein $A^1$ represents a nitrogen atom, $Q^1$ represents an oxygen atom, $Q^2$ are absent, $R^3$ represents a cyclopropyl group, and T represents any substituents described in [Table L1] to [Table L3] (hereinafter, referred to as "Compound Class $SX_{33}$").

A compound (L-1) wherein $A^1$ represents a nitrogen atom, $Q^1$ represents an oxygen atom, $Q^2$ are absent, $R^3$ represents a 1-cyanocyclopropyl group, and T represents any substituents described in [Table L1] to [Table L3] (hereinafter, referred to as "Compound Class $SX_{34}$").

A compound (L-1) wherein $A^1$ represents a nitrogen atom, $Q^1$ represents an oxygen atom, $Q^2$ are absent, $R^3$ represents a chlorine atom, and T represents any substituents described in [Table L1] to [Table L3] (hereinafter, referred to as "Compound Class $SX_{35}$").

A compound (L-1) wherein $A^1$ represents a nitrogen atom, $Q^1$ represents N—CN, $Q^2$ are absent, $R^3$ represents a hydrogen atom, and T represents any substituents described in [Table L1] to [Table L3] (hereinafter, referred to as "Compound Class $SX_{36}$").

A compound (L-1) wherein $A^1$ represents a nitrogen atom, $Q^1$ represents N—CN, $Q^2$ are absent, $R^3$ represents a trifluoromethyl group, and T represents any substituents described in [Table L1] to [Table L3] (hereinafter, referred to as "Compound Class $SX_{37}$").

A compound (L-1) wherein $A^1$ represents a nitrogen atom, $Q^1$ represents N—CN, $Q^2$ are absent, $R^3$ represents a cyclopropyl group, and T represents any substituents described in [Table L1] to [Table L3] (hereinafter, referred to as "Compound Class $SX_{38}$").

A compound (L-1) wherein $A^1$ represents a nitrogen atom, $Q^1$ represents N—CN, $Q^2$ are absent, $R^3$ represents a 1-cyanocyclopropyl group, and T represents any substituents described in [Table L1] to [Table L3] (hereinafter, referred to as "Compound Class $SX_{39}$").

A compound (L-1) wherein $A^1$ represents a nitrogen atom, $Q^1$ represents N—CN, $Q^2$ are absent, $R^3$ represents a chlorine atom, and T represents any substituents described in [Table L1] to [Table L3] (hereinafter, referred to as "Compound Class $SX_{40}$").

A compound (L-1) wherein $A^1$ represents a nitrogen atom, $Q^1$ represents an oxygen atom, $Q^2$ represents N—CN, $R^3$ represents a hydrogen atom, and T represents any substituents described in [Table L1] to [Table L3] (hereinafter, referred to as "Compound Class $SX_{41}$").

A compound (L-1) wherein $A^1$ represents a nitrogen atom, $Q^1$ represents an oxygen atom, $Q^2$ represents N—CN, $R^3$ represents a trifluoromethyl group, and T represents any substituents described in [Table L1] to [Table L3](hereinafter, referred to as "Compound Class $SX_{42}$").

A compound (L-1) wherein $A^1$ represents a nitrogen atom, $Q^1$ represents an oxygen atom, $Q^2$ represents N—CN, $R^3$ represents a cyclopropyl group, and T represents any substituents described in [Table L1] to [Table L3] (hereinafter, referred to as "Compound Class $SX_{43}$").

A compound (L-1) wherein $A^1$ represents a nitrogen atom, $Q^1$ represents an oxygen atom, $Q^2$ represents N—CN, $R^3$ represents a 1-cyanocyclopropyl group, and T represents any substituents described in [Table L1] to [Table L3](hereinafter, referred to as "Compound Class $SX_{44}$").

A compound (L-1) wherein $A^1$ represents a nitrogen atom, $Q^1$ represents an oxygen atom, $Q^2$ represents N—CN, $R^3$ represents a chlorine atom, and T represents any substituents described in [Table L1] to [Table L3] (hereinafter, referred to as "Compound Class $SX_{45}$").

A compound (L-1) wherein $A^1$ represents a nitrogen atom, $Q^1$ and $Q^2$ represent an oxygen atom, $R^3$ represents a hydrogen atom, and T represents any substituents described in [Table L1] to [Table L3] (hereinafter, referred to as "Compound Class $SX_{46}$").

A compound (L-1) wherein $A^1$ represents a nitrogen atom, $Q^1$ and $Q^2$ represent an oxygen atom, $R^3$ represents a trifluoromethyl group, and T represents any substituents described in [Table L1] to [Table L3] (hereinafter, referred to as "Compound Class $SX_{47}$").

A compound (L-1) wherein $A^1$ represents a nitrogen atom, $Q^1$ and $Q^2$ represent an oxygen atom, $R^3$ represents a cyclopropyl group, and T represents any substituents described in [Table L1] to [Table L3] (hereinafter, referred to as "Compound Class $SX_{48}$").

A compound (L-1) wherein $A^1$ represents a nitrogen atom, $Q^1$ and $Q^2$ represent an oxygen atom, $R^3$ represents a 1-cyanocyclopropyl group, and T represents any substituents described in [Table L1] to [Table L3] (hereinafter, referred to as "Compound Class $SX_{49}$").

A compound (L-1) wherein $A^1$ represents a nitrogen atom, $Q^1$ and $Q^2$ represent an oxygen atom, $R^3$ represents a chlorine atom, and T represents any substituents described in [Table L1] to [Table L3] (hereinafter, referred to as "Compound Class $SX_{50}$").

A compound represented by formula (L-2):

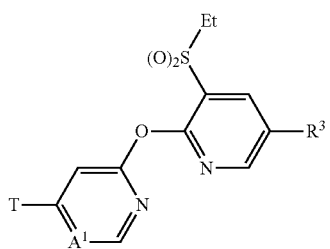

(hereinafter, referred to as "Compound (L-2)") wherein $A^1$ represents CH, T represents a trifluoromethyl group, and $R^3$ represents any substituents described in [Table L4] to [Table L12] (hereinafter, referred to as "Compound Class $SX_{51}$").

Table 3

TABLE L4

F
Br
I
Me
Et
Pr
i-Pr
$CHF_2$
$CH=CH_2$
$CMe=CH_2$
1-F—c-Pr
2,2-$F_2$—c-Pr
c-Bu
c-Pen
c-Hex
1-CN—c-Bu
1-CN—c-Pen
1-CN—c-Hex
CHO
C(O)Me
C(O)c-Pr
C(O)OEt
C(O)$NMe_2$
C(O)NHc-Pr
CH=N—OH
CH=N—OMe
CH=N—OEt
CH=N—$OCH_2CF_3$
CMe=N—OH
CMe=N—OMe
CMe=N—OEt
CMe=N—$OCH_2CF_3$
SEt
S(O)Et
$S(O)_2Et$

TABLE L5

Ph
3-F—Ph
4-F—Ph
3-Cl—Ph
4-Cl—Ph
3-$CF_3$—Ph
4-$CF_3$—Ph
3-$NMe_2$—Ph
4-$NMe_2$—Ph
3-CN—Ph
4-CN—Ph
4-C(O)$NMe_2$—Ph

TABLE L5-continued

4-NHC(O)Me—Ph
3,4-$F_2$—Ph
3,5-$F_2$—Ph
2,4-$F_2$—Ph
3,4,5-$F_3$—Ph
3,4-$Cl_2$—Ph
3,5-$Cl_2$—Ph
3,5-$Cl_2$-4-F—Ph
OPh
O-2-F—Ph
O-3-$CF_3$—Ph
O-4-$CF_3$—Ph
$NH_2$
$NHCH_2CF_3$
NHc-Pr
NH(1-CN—c-Pr)
NHOMe
$NMe_2$
NHC(O)Me
NHC(O)c-Pr
NMeC(O)c-Pr
CN
$NO_2$

TABLE L6

Py2
4-F—Py2
5-F—Py2
4-Cl—Py2
5-Cl—Py2
4-$CF_3$—Py2
5-$CF_3$—Py2
6-$CF_3$—Py2
3-Me—Py2
4-Me—Py2
5-Me—Py2
6-Me—Py2
4-CN—Py2
5-CN—Py2
5-$OCH_2CF_2CF_3$—Py2
3,5-$F_2$—Py2
Py3
6-$CF_3$—Py3
5-$CF_3$—Py3
6-F—Py3
6-Cl—Py3
Py4
OPy2
OPy3
OPy4
O-5-$CF_3$—Py2
O-6-$CF_3$—Py2
OMe
OEt
OPr
Oi-Pr
Oc-Pr
$OCMe_2CN$
$CMe_2CN$
$CMe(CN)_2$

TABLE L7

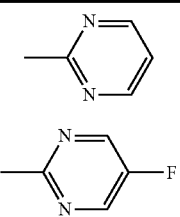

TABLE L7-continued
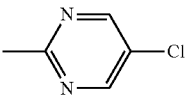
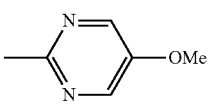
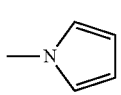
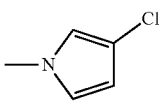
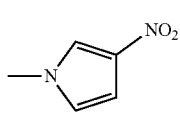
TABLE L8
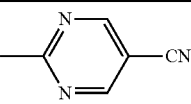
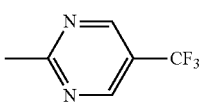
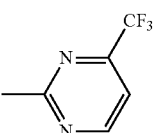
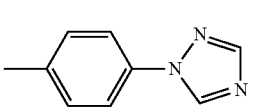
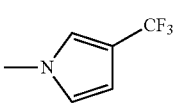
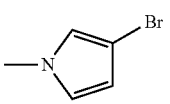
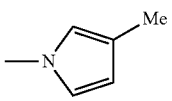
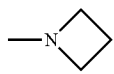
TABLE L9
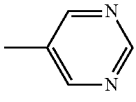
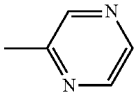
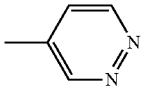
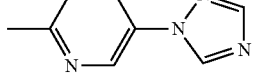
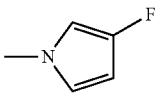
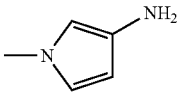
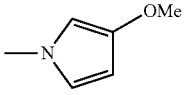
TABLE L10
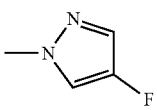
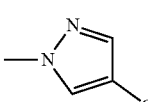
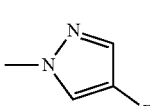
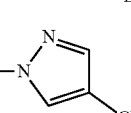
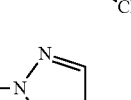

TABLE L10-continued

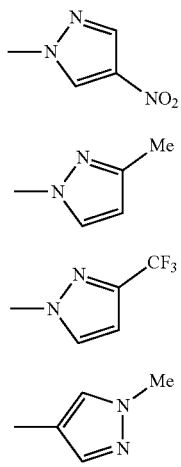

TABLE L11

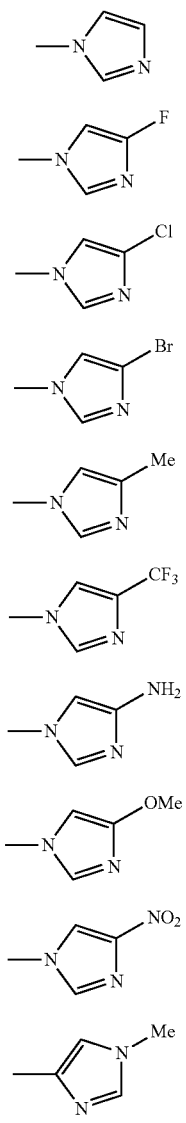

TABLE L12

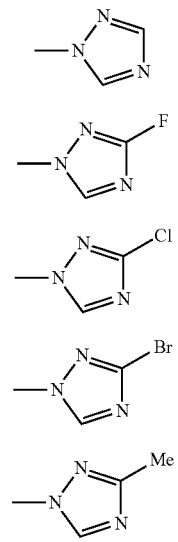

A compound (L-2) wherein $A^1$ represents CH, T represents a perfluorobutyl group, and $R^3$ represents any substituents described in [Table L4] to [Table L12] (hereinafter, referred to as "Compound Class $SX_{52}$").

A compound (L-2) wherein $A^1$ represents CH, T represents a 2,2,3,3-tetrafluoropropoxy group, and $R^3$ represents any substituents described in [Table L4] to [Table L12] (hereinafter, referred to as "Compound Class $SX_{53}$").

A compound (L-2) wherein $A^1$ represents CH, T represents a 2,2,3,3,3-pentafluoropropoxy group, and $R^3$ represents any substituents described in [Table L4] to [Table L12](hereinafter, referred to as "Compound Class $SX_{54}$").

A compound (L-2) wherein $A^1$ represents CH, T represents a 2,2,3,4,4,4-hexafluorobutoxy group, and $R^3$ represents any substituents described in [Table L4] to [Table L12](hereinafter, referred to as "Compound Class $SX_{55}$").

A compound (L-2) wherein $A^1$ represents CH, T represents a 2,2,3,3,4,4,4-heptafluorobutoxy group, and $R^3$ represents any substituents described in [Table L4] to [Table L12](hereinafter, referred to as "Compound Class $SX_{56}$").

A compound (L-2) wherein $A^1$ represents CH, T represents a 2,2,3,3,4,4,5,5,5-nonafluoropenthyloxy group, and R³ represents any substituents described in [Table L4] to [Table L12] (hereinafter, referred to as "Compound Class SX₅₇").

A compound (L-2) wherein A¹ represents CH, T represents a 2-cyano-2-methylpropoxy group, and R³ represents any substituents described in [Table L4] to [Table L12] (hereinafter, referred to as "Compound Class SX₅₈").

A compound (L-2) wherein A¹ represents CH, T represents a (1-cyanocyclopropyl)methoxy group, and R³ represents any substituents described in [Table L4] to [Table L12](hereinafter, referred to as "Compound Class SX₉₅").

A compound (L-2) wherein A¹ represents CH, T represents a 3-(trifluoromethyl)phenyl group, and R³ represents any substituents described in [Table L4] to [Table L12] (hereinafter, referred to as "Compound Class SX₆₀").

A compound (L-2) wherein A¹ represents a nitrogen atom, T represents a trifluoromethyl group, and R³ represents any substituents described in [Table L4] to [Table L12](hereinafter, referred to as "Compound Class SX₆₁").

A compound (L-2) wherein A¹ represents a nitrogen atom, T represents a perfluorobutyl group, and R³ represents any substituents described in [Table L4] to [Table L12](hereinafter, referred to as "Compound Class SX₆₂").

A compound (L-2) wherein A¹ represents a nitrogen atom, T represents a 2,2,3,3-tetrafluoropropoxy group, and R³ represents any substituents described in [Table L4] to [Table L12] (hereinafter, referred to as "Compound Class SX₆₃").

A compound (L-2) wherein A¹ represents a nitrogen atom, T represents a 2,2,3,3,3-pentafluoropropoxy group, and R³ represents any substituents described in [Table L4] to [Table L12] (hereinafter, referred to as "Compound Class SX₆₄").

A compound (L-2) wherein A¹ represents a nitrogen atom, T represents a 2,2,3,4,4,4-hexafluorobutoxy group, and R³ represents any substituents described in [Table L4] to [Table L12] (hereinafter, referred to as "Compound Class SX₆₅").

A compound (L-2) wherein A¹ represents a nitrogen atom, T represents a 2,2,3,3,4,4,4-heptafluorobutoxy group, and R³ represents any substituents described in [Table L4] to [Table L12] (hereinafter, referred to as "Compound Class SX₆₆").

A compound (L-2) wherein A¹ represents a nitrogen atom, T represents a 2,2,3,3,4,4,5,5,5-nonafluoropenthyloxy group, and R³ represents any substituents described in [Table L4] to [Table L12] (hereinafter, referred to as "Compound Class SX₆₇").

A compound (L-2) wherein A¹ represents a nitrogen atom, T represents a 2-cyano-2-methylpropoxy group, and R³ represents any substituents described in [Table L4] to [Table L12] (hereinafter, referred to as "Compound Class SX₆₉").

A compound (L-2) wherein A¹ represents a nitrogen atom, T represents a (1-cyanocyclopropyl)methoxy group, and R³ represents any substituents described in [Table L4] to [Table L12] (hereinafter, referred to as "Compound Class SX₆₉").

A compound (L-2) wherein A¹ represents a nitrogen atom, T represents a 3-(trifluoromethyl)phenyl group, and R³ represents any substituents described in [Table L4] to [Table L12] (hereinafter, referred to as "Compound Class SX₇₀").

A compound represented by formula (L-3):

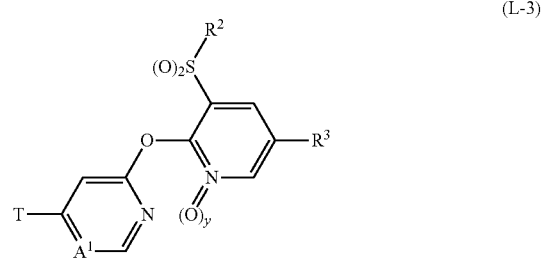

(L-3)

(hereinafter, referred to as "Compound (L-3)")
wherein A¹ represents CH, T represents a 2,2,3,3,3-pentafluoropropoxy group, R² represents a methyl group, n is 0, y is 0, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₁").

A compound (L-3) wherein A¹ represents CH, T represents a 2,2,3,3,3-pentafluoropropoxy group, R² represents a methyl group, n is 0, y is 0, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₂").

A compound (L-3) wherein A¹ represents CH, T represents a 2,2,3,3,3-pentafluoropropoxy group, R² represents a methyl group, n is 2, y is 0, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₃").

A compound (L-3) wherein A¹ represents CH, T represents a 2,2,3,3,3-pentafluoropropoxy group, R² represents a methyl group, n is 2, y is 1, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₄").

A compound (L-3) wherein A¹ represents CH, T represents a 2,2,3,3,3-pentafluoropropoxy group, R² represents an ethyl group, n is 2, y is 1, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₅").

A compound (L-3) wherein A¹ represents a nitrogen atom, T represents a 2,2,3,3,3-pentafluoropropoxy group, R² represents a methyl group, n is 0, y is 0, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₆").

A compound (L-3) wherein A¹ represents a nitrogen atom, T represents a 2,2,3,3,3-pentafluoropropoxy group, R² represents a methyl group, n is 1, y is 0, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class SX₇₇").

A compound (L-3) wherein A¹ represents a nitrogen atom, T represents a 2,2,3,3,3-pentafluoropropoxy group, R² represents a methyl group, n is 2, y is 0, and R³ represents a hydrogen atom, a trifluoromethyl group, a cyclopropyl group, a 1-cyanocyclopropyl group, or any substituents described in [Table L4] to [Table L12] (hereinafter, referred to as "Compound Class $SX_{78}$").

A compound (L-3) wherein $A^1$ represents a nitrogen atom, T represents a 2,2,3,3,3-pentafluoropropoxy group, $R^2$ represents a methyl group, n is 2, y is 1, and $R^3$ represents a hydrogen atom, a trifluoromethyl group, a cyclopropyl group, a 1-cyanocyclopropyl group, or any substituents described in [Table L4] to [Table L12] (hereinafter, referred to as "Compound Class $SX_{79}$").

A compound (L-3) wherein $A^1$ represents a nitrogen atom, T represents a 2,2,3,3,3-pentafluoropropoxy group, $R^2$ represents an ethyl group, n is 2, y is 1, and $R^3$ represents a hydrogen atom, a trifluoromethyl group, a cyclopropyl group, a 1-cyanocyclopropyl group, or any substituents described in [Table L4] to [Table L12] (hereinafter, referred to as "Compound Class $SX_{80}$").

Next, examples of the intermediate compounds which are prepared according to any one of the preparation examples described in Examples and the processes described herein are shown below.

A compound represented by formula (L-4):

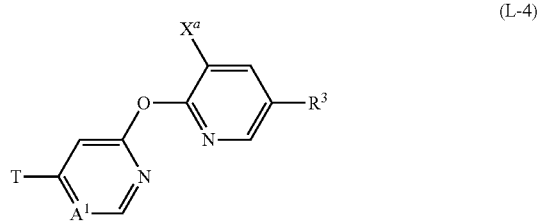

(L-4)

(hereinafter, referred to as "Compound (L-4)") wherein $A^1$ represents CH, $X^a$ represents a fluorine atom, $R^3$ represents a hydrogen atom, and T represents any substituents described in [Table L1] to [Table L3].

A compound represented by formula (L-4) wherein $A^1$ represents CH, $X^a$ represents a fluorine atom, $R^3$ represents a trifluoromethyl group, and T represents any substituents described in [Table L1] to [Table L3].

A compound represented by formula (L-4) wherein $A^1$ represents CH, $X^a$ represents a fluorine atom, $R^3$ represents a cyclopropyl group, and T represents any substituents described in [Table L1] to [Table L3].

A compound represented by formula (L-4) wherein $A^1$ represents CH, $X^a$ represents a fluorine atom, $R^3$ represents a 1-cyanocyclopropyl group, and T represents any substituents described in [Table L1] to [Table L3].

A compound represented by formula (L-4) wherein $A^1$ represents CH, $X^a$ represents a fluorine atom, $R^3$ represents a chlorine atom, and T represents any substituents described in [Table L1] to [Table L3].

A compound represented by formula (L-4) wherein $A^1$ represents CH, $X^a$ represents a chlorine atom, $R^3$ represents a hydrogen atom, and T represents any substituents described in [Table L1] to [Table L3].

A compound represented by formula (L-4) wherein $A^1$ represents CH, $X^a$ represents a chlorine atom, $R^3$ represents a trifluoromethyl group, and T represents any substituents described in [Table L1] to [Table L3].

A compound represented by formula (L-4) wherein $A^1$ represents CH, $X^a$ represents a chlorine atom, $R^3$ represents a cyclopropyl group, and T represents any substituents described in [Table L1] to [Table L3].

A compound represented by formula (L-4) wherein $A^1$ represents CH, $X^a$ represents a chlorine atom, $R^3$ represents a 1-cyanocyclopropyl group, and T represents any substituents described in [Table L1] to [Table L3].

A compound represented by formula (L-4) wherein $A^1$ represents CH, $X^a$ represents a chlorine atom, $R^3$ represents a chlorine atom, and T represents any substituents described in [Table L1] to [Table L3].

A compound represented by formula (L-4) wherein $A^1$ represents CH, $X^a$ represents a fluorine atom, $R^3$ represents a hydrogen atom, and T represents any substituents described in [Table L1] to [Table L3].

A compound represented by formula (L-4) wherein $A^1$ represents a nitrogen atom, $X^a$ represents a fluorine atom, $R^3$ represents a trifluoromethyl group, and T represents any substituents described in [Table L1] to [Table L3].

A compound represented by formula (L-4) wherein $A^1$ represents a nitrogen atom, $X^a$ represents a fluorine atom, $R^3$ represents a cyclopropyl group, and T represents any substituents described in [Table L1] to [Table L3].

A compound represented by formula (L-4) wherein $A^1$ represents a nitrogen atom, $X^a$ represents a fluorine atom, $R^3$ represents a 1-cyanocyclopropyl group, and T represents any substituents described in [Table L1] to [Table L3].

A compound represented by formula (L-4) wherein $A^1$ represents a nitrogen atom, $X^a$ represents a fluorine atom, $R^3$ represents a chlorine atom, and T represents any substituents described in [Table L1] to [Table L3].

A compound represented by formula (L-4) wherein $A^1$ represents a nitrogen atom, $X^a$ represents a chlorine atom, $R^3$ represents a hydrogen atom, and T represents any substituents described in [Table L1] to [Table L3].

A compound represented by formula (L-4) wherein $A^1$ represents a nitrogen atom, $X^a$ represents a chlorine atom, $R^3$ represents a trifluoromethyl group, and T represents any substituents described in [Table L1] to [Table L3].

A compound represented by formula (L-4) wherein $A^1$ represents a nitrogen atom, $X^a$ represents a chlorine atom, $R^3$ represents a cyclopropyl group, and T represents any substituents described in [Table L1] to [Table L3].

A compound represented by formula (L-4) wherein $A^1$ represents a nitrogen atom, $X^a$ represents a chlorine atom, $R^3$ represents a 1-cyanocyclopropyl group, and T represents any substituents described in [Table L1] to [Table L3].

A compound represented by formula (L-4) wherein $A^1$ represents a nitrogen atom, $X^a$ represents a chlorine atom, $R^3$ represents a chlorine atom, and T represents any substituents described in [Table L1] to [Table L3].

Next, the Formulation Examples of the present compound are shown below. The "parts" represents "part by weight" Further, the present compound S represents the compounds described as the Compound Class $SX_1$ to $SX_{80}$.

Formulation Example 1

Into a mixture of 10 parts of any one of the present compounds S, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of wet process silica, and 54 parts of diatomaceous earth are mixed, and further 20 parts of any one of the present compounds S is added thereto, followed by mixing them to obtain each formulation.

Formulation Example 3

To 2 parts of any one of the present compounds S, 1 part of wet process silica, 2 parts of calcium lignin sulfonate, 30 parts of bentonite, and 65 parts of kaolin clay are added, followed by mixing them. To the mixture is then added an appropriate amount of water, and the mixture are further stirred, granulated with a granulator, and forced-air dried to obtain each formulation.

Formulation Example 4

Into an appropriate amount of acetone, 1 part of any one of the present compounds S is mixed, and then 5 parts of wet process silica, 0.3 parts of isopropyl acid phosphate, and 93.7 parts of kaolin clay are added, following by mixing them with stirring thoroughly and removal of acetone from the mixture by evaporation to obtain each formulation.

Formulation Example 5

A mixture of 35 parts of polyoxyethylene alkyl ether sulfate ammonium salt and wet process silica (weight ratio of 1:1), 20 parts of any one of the present compounds S, and 45 parts of water are enough mixed to obtain each formulation.

Formulation Example 6

Ten (10) parts of any one of the present compound S, 18 parts of benzyl alcohol 18 parts and 9 parts of DMSO are mixed, and 6.3 parts of GERONOL (registered trademark) TE250, 2.7 parts of Ethylan (registered trademark) NS-500LQ, and 54 parts of solventnaphtha are added thereto, and then mixed to obtain each formulation.

Formulation Example 7

Into a mixture of 5 parts of xylene and 5 parts of trichloroethane, 0.1 parts of any one of the present compounds S are mixed, and the resulting mixture is then mixed with 89.9 parts of kerosene to obtain each solution.

Formulation Example 8

Into 0.5 ml of acetone, 10 mg of any one of the present compounds S is mixed, and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 9

Into an aerosol can, 0.1 parts of any one of the present compounds S and 49.9 parts of Neothiozole (manufactured by Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 10

A mixture of 0.6 parts of any one of the present compounds S, 0.01 parts of 2,6-di-tert-butyl-4-methylphenol, 5 parts of xylene, 3.39 parts of kerosene, and 1 part of Rheodol (registered trademark) MO-60, and 50 parts of distilled water are filled into an aerosol container, and a valve part of the container is attached. Then, 40 parts of LPG is filled therein through the valve under pressure to obtain each aqueous aerosol.

Formulation Example 11

Zero point one (0.1) g of any one of the present compounds S is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 12

Five (5) parts of any one of the present compounds S, and 95 parts of ethylene-methyl methacrylate copolymer (the ratio of the methyl methacrylate in the copolymer: 10 weight %) are melted and kneaded, and the resulting kneaded product is extruded from an extrusion molding machine to obtain each rod-shaped molded product having a length of 15 cm and a diameter of 3 mm.

Formulation Example 13

Five (5) parts of any one of the present compounds S, and 95 parts of plasticized polyvinyl chloride resin are melted and kneaded, and the resulting kneaded product is extruded from an extrusion molding machine to obtain each rod-shaped molded product having a length of 15 cm and a diameter of 3 mm.

Formulation Example 14

One-hundred (100) mg of any one of the present compounds S, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixture are compressed to an appropriate size to obtain each tablet.

Formulation Example 15

Twenty-five (25) mg of any one of the present compounds S, 60 mg of lactose, 25 mg of corn starch, 6 mg of carmellose calcium, and an appropriate amount of 5% aqueous hydroxypropyl methylcellulose solution are mixed, and the resulting mixture are filled into a hard shell gelatin capsule or a hydroxypropyl methylcellulose capsule to obtain each capsule.

Formulation Example 16

To 100 mg of any one of the present compounds S, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum (registered trademark) K (manufactured by Vanderbilt Co.), 35 mg of a perfume, and 500 mg of a coloring agent, distilled water is added so that a final volume is set to be 100 mL, followed by mixing the mixture to obtain each suspension for oral administration.

Formulation Example 17

Into a mixture of 5 parts of an emulsifier, 3 parts of benzyl alcohol and 30 parts of propylene glycol, 5 parts of any one of the present compounds S is mixed, and phosphate buffer is added thereto so that a pH of the solution is set to be 6.0 to 6.5, and water is added as the rest parts to obtain each solution for oral administration.

Formulation Example 18

To a mixture of 57 parts of fractional distillated palm oil and 3 parts of polysorbate 85, 5 parts of aluminium distearate is added, and heated to disperse it. The resulting mixture is cooled to room temperature, and 25 parts of saccharin is dispersed in an oil vehicle. Ten (10) parts of any one of the present compounds S is divided thereto to obtain each paste for oral administration.

Formulation Example 19

Five (5) parts of any one of the present compounds S is mixed with 95 parts of limestone filler, followed by a wet-granulation of the resulting mixture to obtain each granule for oral administration.

Formulation Example 20

Into 80 parts of diethylene glycol monoethyl ether, 5 parts of any one of the present compounds S is mixed, and 15 parts of propylene carbonate is added thereto, and the resulting mixture is mixed to obtain each spot-on solution.

Formulation Example 21

Into 70 parts of diethylene glycol monoethyl ether, 10 parts of any one of the present compounds S is mixed, and 20 parts of 2-octyldodecanol is added thereto, and the resulting mixture is mixed to obtain each pour-on solution.

Formulation Example 22

To 0.1 parts of any one of the present compounds S, 40 parts of sodium polyoxyethylene laurylether sulfate (25% aqueous solution), 5 parts of lauramidopropyl betaine, 5 parts of coconut fatty acid monoethanolamide, 0.5 parts of carboxy vinyl polymer, and 49.4 parts of purified water are added, and the resulting mixture is enough mixed to obtain each shampoo formulation.

Formulation Example 23

Zero point fifteen (0.15) parts of any one of the present compounds S, 95 parts of animal feed, as well as 4.85 parts of a mixture of dibasic calcium phosphate, diatomaceous earth, Aerosil (registered trademark), and carbonate (or chalk) are enough mixed to obtain each premix for animal feed.

Formulation Example 24

Seven point two (7.2) g of any one of the present compounds S, and 92.8 g of Hosco (registered trademark) S-55 are mixed at 100° C., and the resulting mixture is poured into a suppository mold, followed by performing a cooling solidification to obtain each suppository.

Next, Test Examples are used to show an efficacy of the Present compound on controlling harmful arthropods.

The following test examples were carried out at 25° C.

Test Method 1

The test compounds is made to a formulation according to a similar method to that described in the Formulation Example 5, and thereto is added water containing 0.03 v/v % of a spreader to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all stages of life) are released onto the leaves of the cucumber. After 1 day, the diluted solutions are sprayed into the seedling in a ratio of 10 mL/seedling. Further, after 5 days, the number of the surviving insects is examined and the controlling value is calculated by the following equation.

Controlling value (%)={1−($Cb \times Tai$)/($Cai \times Tb$)}×100 wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

Test Example 1

The test was conducted by making the prescribed concentration 500 ppm and using the below-mentioned Present compounds as a test compound according to the test method 1. As a result of the test, the below-mentioned Present compounds X showed 90% or greater as the controlling value.

Present compound: 4, 5, 7, 12, 17, 18, 19, 20, 21, 23, 24 and 28

Test Method 2

The test compounds are made to a formulation according to a similar method to that described in the Formulation Example 5, and thereto is added water containing 0.03 v/v % of a spreader to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 3rd instar larvae of brown planthoppers (*Nilaparvata lugens*) are released onto the rice leaves. After 6 days, the morality is calculated by the following equation.

Morality (%)={1−the number of the surviving insects/20}×100

Test Example 2

The test can be conducted by making the prescribed concentration 500 ppm and using the Present compounds as a test compound according to the test method 2 so as to confirm the effect.

Test Method 3

The test compounds are made to a formulation according to a similar method to that described in the Formulation Example 5, and thereto is added water containing 0.03 v/v % of a spreader to prepare a diluted solution containing a prescribed concentration of the test compound.

Silverleaf whiteflies (*Bemisia tabaci*) are released on tomato (*Lycopersicon esculentum*) seedling that is planted in the container, and then spawn for about 24 hours. The seedling are stored for 8 days, and the larvae of silverleaf whiteflies are hatched from the laid eggs. The diluted solutions are sprayed into the seedling in a ratio of 10 mL/seedling. After 7 days, the number of the surviving insects is examined, and the controlling value is calculated by the following equation.

Controlling value (%)={1−(Cb×Tai)/(Cai×Tb)}×100 wherein the symbols in the formula represent the following descriptions.
- Cb: Number of the insects shortly before the treatment in untreated group;
- Cai: Number of the surviving insects at the time of the investigation in untreated group;
- Tb: Number of the insects shortly before the treatment in treated group;
- Tai: Number of the surviving insects at the time of the investigation in treated group;

Here the "untreated group" represents a group where the similar treatment procedure to that of the treated group except not using the test compound is done.

Test Example 3

The test can be conducted by making the prescribed concentration 500 ppm and using the Present compounds as a test compound according to the test method 3 so as to confirm the effect.

Test Method 4

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) diamondback moth (*Plutella xylostella*) at the second instar larval stage are released into the cup. After 5 days, the number of the surviving insects is counted, and the mortality of insects is calculated by the following equation.

Mortality (%)=(1−Number of surviving insects/5)×100

Test Example 4

The test was conducted by making the prescribed concentration 500 ppm and using the below-mentioned Present compounds as a test compound according to the test method 4. As a result of the test, the below-mentioned Present compound showed 80% or greater as the mortality of insects.

Present compound: 2, 4, 5, 7, 10, 12, 15, 18, 21, 24, and 28

Test Method 5

Test compounds are made to a formulation according to a similar method to that described in the Formulation example 5, and thereto is added water containing 0.03 v/vs of Shindain (registered trademark) to prepare a diluted solution containing a prescribed concentration of the test compound.

Cabbage (*Brassicae oleracea*) seedling (on the developmental stage of the third to fourth true leaf) is planted in a cup, and the diluted solutions are sprayed into the seedling at a ratio of 20 mL/seedling. Thereafter, 10 cotton worm (*Spodoptera litura*) at the third instar larval stage are released. After 6 days, the number of the surviving insects is counted, and the mortality of insects is calculated by the following equation.

Mortality (%)=(1−Number of surviving insects/10)×100

Test Example 5

The test was conducted by making the prescribed concentration 500 ppm and using the below-mentioned Present compounds as a test compound according to the test method 5. As a result of the test, the below-mentioned Present compound showed 80% or greater as the mortality of insects.

Present compound: 5 and 19

Test Method 6

Test compounds are made to a formulation according to a similar method to that described in the Formulation example 5, and thereto is added water to prepare a diluted solution containing a prescribed concentration of the test compound.

A filter paper having a diameter of 5.5 cm in diameter is spread on the bottom of the cup, and then 0.7 ml of the diluted solutions are added dropwise to the filter paper and 30 mg of sucrose is uniformly placed on the filter paper as a bait. Ten (10) housefly (*Musca domestica*) female adults are released into the cup, and the cup is then covered with the lid. After 24 hours, the number of the dead insects is examined, and the mortality of insects is calculated by the following equation.

Mortality (%)=(Number of dead insects/Number of tested insects)×100

Test Example 6

The test was conducted by making the prescribed concentration 500 ppm and using the below-mentioned Present compounds as a test compound according to the test method 6. As a result of the test, the below-mentioned Present compound showed 80% or greater as the mortality of insects.

Present compound: 14

Test Method 7

Test compounds are made to a formulation according to a similar method to that described in the Formulation example 5, and thereto is added water to prepare a diluted solution containing a prescribed concentration of the test compound.

Into the diluted solution, 30 common house mosquito (*Culex pipiens pallens*) at the last instar larval stage are released, and after 1 day, the state of the house mosquito larvae is examined, and the mortality of insects is calculated by the following equation.

Mortality (%)=(Number of dead insects/Number of tested insects)×100

Test Example 7

The test was conducted by making the prescribed concentration 3.5 ppm and using the below-mentioned Present compounds as a test compound according to the test method 7. As a result of the test, the below-mentioned Present compound showed 91% or greater as the mortality of insects.

Present compound: 2, 15, 17 and 18

Test Method 8

Each 1 mg of the test compounds is dissolved into 50 μL of a mixed solution of polyoxyethylene sorbitan mono-cocoate and acetone (polyoxyethylene sorbitan mono-cocoate:acetone=5:95 (v/v ratio)). Thereto is added water containing 0.03% by volume of Shindain (registered trademark) to prepare a diluted solution containing a prescribed concentration of the test compound.

A young entire seedling of Corns (*Zea mays*) is immersed into the diluted solution for 30 seconds. Thereafter, each two grains of the seedlings are installed in a plastic petri dish (90 mm radius), and 10 Western corn rootworms (*Diabrotica virgifera virgifera*) at the second instar larval stage are released into the dish. After 5 days, the number of the dead insects is counted, and the mortality of insects is calculated by the following equation.

Mortality (%)=(Number of dead insects/10)×100

Test Example 8

The test was conducted by making the prescribed concentration 500 ppm and using the below-mentioned Present compounds as a test compound according to the test method 8. As a result of the test, the below-mentioned Present compound showed 80% or greater as the mortality of insects.

Present compound: 2 and 17

Test Method 9

Each 1 mg of the present compound is dissolved into 10 μL of a mixed solution of xylene, DMF, and a surfactant (xylene:DMF:surfactant=4:4:1 (v/v ratio)). Thereto is added water containing 0.02% by volume of a spreader to prepare diluted solution A containing a prescribed concentration of the present compound.

Each 1 mg of the present ingredients is dissolved into 10 μL of a mixed solution of xylene, DMF, and a surfactant (xylene:DMF:surfactant=4:4:1 (v/v ratio)). Thereto is added water containing 0.02% by volume of a spreader to prepare diluted solution B containing a prescribed concentration of the present ingredient.

The diluted solution A is mixed with the diluted solution B to prepare diluted solution C.

Leaf discs of Cucumber (*Cucumber sativus*) cotyledon (length 1.5 cm) are placed in each well of 24-well microplate. Two (2) apterous adults and 8 larvae of cotton aphids (*Aphis gossypii*) per one well are released and the diluted solution C is sprayed at 20 μL per one well. The group is defined as "treated group". A well that is sprayed with 20 μL of water containing 0.02% by volume of a spreader instead of the diluted solution C is defined as "untreated group".

After drying the diluted solution C, the upper microplate is covered with a film sheet. After 5 days, the number of the surviving insects in each well is examined.

The controlling value is calculated by the following equation.

Controlling value (%)={1−(Tai)/(Cai)}×100 wherein the symbols in the equation represent the following descriptions.

Cai: Number of the surviving insects at the time of the examination in untreated group;

Tai: Number of the surviving insects at the time of the examination in treated group.

Specific diluted solutions C, which can confirm their effect according to the Test method 9, are described in the following 1) to 5).

1) The diluted solution C comprises the combination recited in List A wherein a concentration of the present compound is 200 ppm and a concentration of the present ingredient is 2000 ppm. In List A, Comp X represents any one compound selected from the present compounds 1 to 28.

List A:

Comp X+Clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA11; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the present compound is 200 ppm, and a concentration of the present ingredient is 200 ppm.

3) The diluted solution C comprises the combination recited in List A wherein a concentration of the present compound is 500 ppm, and a concentration of the present ingredient is 50 ppm.

4) The diluted solution C comprises the combination recited in List A wherein a concentration of the present compound is 500 ppm, and a concentration of the present ingredient is 5 ppm.

5) The diluted solution C comprises the combination recited in List A wherein a concentration of the present compound is 500 ppm, and a concentration of the present ingredient is 0.5 ppm.

INDUSTRIAL APPLICABILITY

The present compound shows an excellent control effect against a harmful arthropod.

The invention claimed is:
1. A compound represented by formula (I) or its N oxide compound:

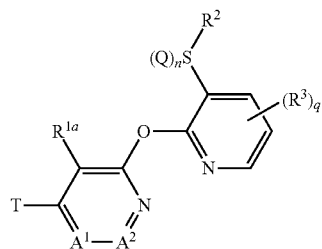

(1)

wherein
a combination of $A^1$ and $A^2$ represents
a combination wherein $A^1$ represents a nitrogen atom or $CR^{1b}$ and $A^2$ represents $CR^{1c}$; or
a combination wherein $A^1$ represents $CR^{1b}$ and $A^2$ represents a nitrogen atom,
$R^{1a}$, $R^{1b}$ and $R^{1c}$ are identical to or different from each other and each represents a C1-C6 alkyl group which may be optionally substituted with one or more halogen atoms, a C1-C6 alkoxy group which may be optionally substituted with one or more halogen atoms, a C1-C6 alkylamino group which may be optionally substituted with one or more halogen atoms, a di(C1-C4 alkyl) amino group which may be optionally substituted with one or more halogen atoms, a hydroxy group, an amino group, a nitro group, a cyano group, a halogen atom, or a hydrogen atom,
$R^2$ represents a C1-C6 alkyl group which may be optionally substituted with one or more halogen atoms, a cyclopropyl group, or a cyclopropylmethyl group,
n is 0, 1 or 2,
q is 0, 1, 2 or 3,
$R^3$ each represents a C1-C6 chain hydrocarbon group which may be optionally substituted with one or more substituents selected from Group A, a C3-C7 cycloalkyl group which may be optionally substituted with one or more substituents selected from Group B, a phenyl group which may be optionally substituted with one or more substituents selected from Group C, a five or six membered aromatic heterocyclic group which may be optionally substituted with one or more substituents selected from Group C, a three to seven membered nonaromatic heterocyclic group which may be optionally substituted with one or more substituents selected from Group B, $OR^8$, $NR^7R^8$, $NR^7NR^8R^9$, $NR^7OR^9$, $NR^7C(O)R^{10}$, $NR^7C(O)OR^{11}$, $N=CHNR^7R^9$, $C(O)R^{10}$, $C(O)OR^{10}$, $C(O)NR^7R^8$, $CR^7=NOR^9$, $S(O)_pR^{12}$, a cyano group, a nitro group, or a halogen atom, and when q is 2 or 3, a plural of $R^3$ may be identical to or different from each other,
p is 0, 1 or 2,
Q represents an oxygen atom or $NR^4$, and when n is 2, two Q may be identical to or different from each other,
$R^4$ represents a C1-C6 alkyl group which may be optionally substituted with one or more halogen atoms, a C2-C7 alkylcarbonyl group which may be optionally substituted with one or more halogen atoms, a C2-C7 alkoxycarbonyl group which may be optionally substituted with one or more halogen atoms, a cyano group, a nitro group, or a hydrogen atom, T represents a C1-C10 chain hydrocarbon group which is substituted with one or more halogen atoms, $OR^6$, $S(O)_mR^6$, $OS(O)_2R^6$, $NR^6R^7$, a group represented by formula $T^1$, a group represented by formula $T^2$, or a group represented by formula $T^3$,

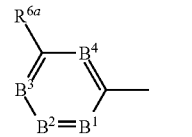

T1

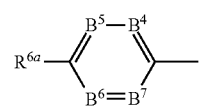

T2

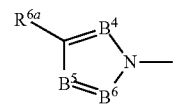

T3 a combination of $B^1$, $B^2$ and $B^3$ represents
a combination wherein $B^1$ represents $CR^{5a}$, $B^2$ represents a nitrogen atom or $CR^{5b}$, and $B^3$ represents a nitrogen atom or $CR^{5c}$; or
a combination wherein B1 represents a nitrogen atom, $B^2$ represents $CR^{5b}$, and $B^3$ represents a nitrogen atom or $CR^{5c}$; or
a combination wherein B1 and $B^2$ represent a nitrogen atom, and $B^3$ represents $CR^{5c}$,
$B^4$ represents a nitrogen atom or $CR^{5d}$,
$B^5$ represents a nitrogen atom or $CR^{5e}$,
$B^6$ represents a nitrogen atom or $CR^{5f}$,
$B^7$ represents a nitrogen atom or $CR^{5g}$,
$R^{5a}$, $R^{5b}$, $R^{5c}$, $R^{5d}$, $R^{5e}$, $R^{5f}$ and $R^{5g}$ are identical to or different from each other and each represent a C1-C6 chain hydrocarbon group which may be optionally substituted with one or more halogen atoms, a C3-C6 cycloalkyl group which may be optionally substituted with one or more halogen atoms, a halogen atom, or a hydrogen atom,
$R^{6a}$ represents a C1-C5 chain hydrocarbon group which is substituted with one or more halogen atoms, $OR^{12}$, $OS(O)_2R^{12}$, $S(O)_mR^{12}$, or a halogen atom,
m is 0, 1 or 2,
$R^{12}$ represents a C1-C6 chain hydrocarbon group which is substituted with one or more halogen atoms,
$R^6$ represents a C1-C10 chain hydrocarbon group which is substituted with one or more substituents selected from the group consisting of cyano group and halogen atom; or a (C3-C7 cycloalkyl) C1-C3 alkyl group which is substituted with one or more substituents selected from the group consisting of cyano group, halogen atom and C1-C6 haloalkyl group,
$R^7$ and $R^9$ are identical to or different from each other and each represent a C1-C6 chain hydrocarbon group which may be optionally substituted with one or more halogen atoms, or a hydrogen atom,
$R^8$ represents a C1-C6 chain hydrocarbon group which may be optionally substituted with one or more substituents selected from Group A, a C3-C7 cycloalkyl group which may be optionally substituted with one or more substituents selected from Group B, a phenyl group which may be optionally substituted with one or more substituents selected from Group C, a five or six membered aromatic heterocyclic group which may be optionally substituted with one or more substituents selected from Group C, a C1-C6 alkylsulfonyl group which may be optionally substituted with one or more halogen atoms, or a hydrogen atom, $R^{10}$ represents a C1-C6 chain hydrocarbon group which may be optionally substituted with one or more halogen atoms, a C3-C7 cycloalkyl group which may be optionally substituted with one or more halogen atoms, a (C3-C6 cycloalkyl) C1-C3 alkyl group which may be optionally substituted with one or more halogen atoms, a phenyl group which may be optionally substituted with one or more substituents selected from Group C, a five or six membered aromatic heterocyclic group which may be optionally substituted with one or more substituents selected from Group C, or a hydrogen atom, $R^{11}$ represents a C1-C6 chain hydrocarbon group which may be optionally substituted with one or more halogen atoms, a C3-C7 cycloalkyl group which may be optionally substituted with one or more halogen atoms, a (C3-C6 cycloalkyl) C1-C3 alkyl group which may be optionally substituted with one or more halogen atoms, a phenyl group which may be optionally substituted with one or more substituents selected from Group C, or a five or six membered aromatic heterocyclic group which may be optionally substituted with one or more substituents selected from Group C, Group A is the group consisting of a C1-C6 alkoxy group which may be optionally substituted with one or more halogen atoms, a C3-C6 alkenyloxy group which may be optionally substituted with one or more halogen atoms, a C3-C6 alkynyloxy group which may be optionally substituted with one or more halogen atoms, a C1-C6 alkylsulfanyl group which may be optionally substituted with one or more halogen atoms, a C1-C6 alkylsulfinyl group which may be optionally substituted with one or more halogen atoms, a C1-C6 alkylsulfonyl group which may be optionally substituted with one or more halogen atoms, a C1-C6 alkylamino group which may be optionally substituted with one or more halogen atoms, a di(C1-C4 alkyl)amino group which may be optionally substituted with one or more halogen atoms, a C3-C6 cycloalkyl group which may be optionally substituted with one or more halogen atoms, a phenyl group, a five or six membered aromatic heterocyclic group, an amino group, a cyano group, a hydroxy group, a sulfanyl group, and a halogen atom, wherein the phenyl group and the five or six membered aromatic heterocyclic group may be optionally substituted with one or more substituents selected from the group consisting of C1-C6 alkyl group which may be optionally substituted with one or more halogen atoms, C1-C6 alkoxy group which may be optionally substituted with one or more halogen atoms, cyano group, nitro group, and halogen atom, Group B is the group consisting of a C1-C6 alkyl group which may be optionally substituted with one or more halogen atoms, a halogen atom, and a cyano group, and Group C is the group consisting of a C1-C6 alkyl group which may be optionally substituted with one or more halogen atoms, a C1-C6 alkoxy group which may be optionally substituted with one or more halogen atoms, a C3-C6 alkenyloxy group which may be optionally substituted with one or more halogen atoms, a C3-C6 alkynyloxy group which may be optionally substituted with one or more halogen atoms, a C1-C6 alkylsulfanyl group which may be optionally substituted with one or more halogen atoms, a C1-C6 alkylsulfinyl group which may be optionally substituted with one or more halogen atoms, a C1-C6 alkylsulfonyl group which may be optionally substituted with one or more halogen atoms, a C1-C6 alkylamino group which may be optionally substituted with one or more halogen atoms, a di(C1-C4 alkyl)amino group which may be optionally substituted with one or more halogen atoms, a C2-C7 alkylcarbonyl group which may be optionally substituted with one or more halogen atoms, a C2-C7 alkoxycarbonyl group which may be optionally substituted with one or more halogen atoms, an amino group, a cyano group, a nitro group, a hydroxy group, a sulfanyl group, and a halogen atom.

2. The compound according to claim 1 or its N oxide compound wherein $A^1$ represents a nitrogen atom or CH, $A^2$ represents CH, and Q represents an oxygen atom.

3. The compound according to claim 1 or its N oxide compound wherein $A^1$ and $A^2$ represent CH, and Q represents an oxygen atom.

4. The compound according to claim 1 or its N oxide compound wherein T represents $OR^6$.

5. The compound according to claim 4 or its N oxide compound wherein $R^6$ represents a C2-C5 alkyl group which is substituted with one or more halogen atoms.

6. A composition for controlling a harmful arthropod comprising the compound according to claim 1 or its N oxide compound.

7. A composition which comprises one or more ingredients selected from the group consisting of the following Groups (a), (b), (c) and (d), and the compound according to claim 1 or its N oxide compound:

Group (a): a group consisting of insecticidal ingredients, miticidal ingredients, and nematicidal ingredients;

Group (b): fingicidal ingredients:

Group (c): plant growth modulating ingredients; and

Group (d): repellent ingredients.

8. A method for controlling a harmful arthropod, which comprises applying an effective amount of the compound according to claim 1 or its N oxide compound to a harmful arthropod or a habitat where the harmful arthropod lives.

9. A seed or vegetative reproductive organ carrying an effective amount of the compound according to claim 1.

10. A method for controlling a harmful arthropod, which comprises applying an effective amount of the composition according to claim 7 to a harmful arthropod or a habitat where the harmful arthropod lives.

11. A seed or vegetative reproductive organ carrying an effective amount of the composition according to claim 7.

* * * * *